(12) United States Patent
Spencer et al.

(10) Patent No.: US 11,076,774 B2
(45) Date of Patent: Aug. 3, 2021

(54) DEVICE WITH FLOW RATE INDICATOR

(71) Applicant: CLEMENT CLARKE INTERNATIONAL LTD., Essex (GB)

(72) Inventors: David Spencer, Harlow (GB); Ronald Bruin, Harlow (GB); Mark Sanders, Dunstable (GB)

(73) Assignee: CLEMENT CLARKE INTERNATIONAL LTD., Essex (GB)

(*) Notice: Subject to any disclaimer, the term of this patent is extended or adjusted under 35 U.S.C. 154(b) by 353 days.

(21) Appl. No.: 16/072,389

(22) PCT Filed: Feb. 10, 2017

(86) PCT No.: PCT/EP2017/053059
§ 371 (c)(1),
(2) Date: Jul. 24, 2018

(87) PCT Pub. No.: WO2017/140599
PCT Pub. Date: Aug. 24, 2017

(65) Prior Publication Data
US 2019/0069806 A1    Mar. 7, 2019

(30) Foreign Application Priority Data

Feb. 15, 2016 (GB) .................................... 1602639
Jan. 10, 2017 (GB) .................................... 1700412

(51) Int. Cl.
*A61B 5/087*    (2006.01)
*A61M 15/00*    (2006.01)

(52) U.S. Cl.
CPC ............. *A61B 5/087* (2013.01); *A61M 15/00* (2013.01); *A61M 15/003* (2014.02);
(Continued)

(58) Field of Classification Search
CPC .. A61B 5/087; A61M 15/003; A61M 15/0041; A61M 15/00; A61M 15/009;
(Continued)

(56) References Cited

U.S. PATENT DOCUMENTS 3,837,341 A * 9/1974 Bell .................. A61M 15/0033
128/203.15
9,138,167 B1 9/2015 Leydon
(Continued)

FOREIGN PATENT DOCUMENTS

GB    2 148 003 A    5/1985
GB    2 372 704 A    9/2002
(Continued)

OTHER PUBLICATIONS

International Search Report issued in International Application No. PCT/EP2017/053057, dated Apr. 26, 2017.
Written Opinion of the International Searching Authority issued in International Application No. PCT/EP2017/053057, dated Apr. 26, 2017.
(Continued)

*Primary Examiner* — Joseph D. Boecker
*Assistant Examiner* — Thomas W Greig
(74) *Attorney, Agent, or Firm* — Charles C. Achkar; Ostrolenk Faber LLP

(57) ABSTRACT

The present invention provides a patient inhalation/exhalation device such as a spirometer, respiratory inhaler or spacer, the device comprising: at least one aperture for inlet or outlet of air into/from the device; a mouthpiece for communication with the mouth of the patient; and a body defining an air flow path extending between the aperture and the mouthpiece along which air is drawn to the mouthpiece by inhalation by the patient or air is forced towards the aperture by exhalation by the patient. The body comprises an air flow rate indicator operable to generate a sound signal to indicate when the air flow rate along the air flow path is at or above a predetermined minimum level. In another aspect,
(Continued)

the present invention provides a device for indicating a desired fluid flow rate along a fluid flow path through a respiratory inhaler. The device comprises an inlet aperture, an outlet aperture for fluid communication with the fluid flow path through the respiratory inhaler, and a body defining a second fluid flow path extending between the inlet aperture and the outlet aperture. The body comprises a connector portion for connection to the respiratory inhaler and a fluid flow rate indicator operable to generate a sound signal to indicate when the fluid flow rate along the second fluid flow path is at a predetermined fluid flow rate. The air flow rate indicators comprise a corrugated portion having at least one or a plurality of corrugations extending into their fluid flow paths.

18 Claims, 9 Drawing Sheets

(52) U.S. Cl.
CPC ...... *A61M 15/009* (2013.01); *A61M 15/0041* (2014.02); *A61M 15/0023* (2014.02); *A61M 2202/064* (2013.01); *A61M 2205/3334* (2013.01); *A61M 2205/3375* (2013.01); *A61M 2205/43* (2013.01); *A61M 2205/502* (2013.01); *A61M 2205/52* (2013.01); *A61M 2205/581* (2013.01)

(58) Field of Classification Search
CPC .......... A61M 15/0023; A61M 15/0001; A61M 2205/43; A61M 2205/3375; A61M 2205/3334; A61M 2205/183; A61M 2205/186
See application file for complete search history.

(56) References Cited

U.S. PATENT DOCUMENTS

| | | |
|---|---|---|
| 2003/0199780 A1 | 10/2003 | Page |
| 2004/0089300 A1* | 5/2004 | Miyamoto ........ A61M 15/0028 128/203.15 |
| 2006/0107755 A1 | 5/2006 | Kuo et al. |
| 2007/0272235 A1* | 11/2007 | Miyamoto ........ A61M 15/0021 128/200.14 |
| 2013/0068221 A1* | 3/2013 | Mian ................ A61M 16/06 128/202.22 |
| 2013/0151162 A1* | 6/2013 | Harris ............... A61M 16/0051 702/19 |
| 2015/0126889 A1 | 5/2015 | Frey et al. |
| 2016/0049096 A1 | 2/2016 | Bruin et al. |

FOREIGN PATENT DOCUMENTS

| | | |
|---|---|---|
| GB | 2 490 770 A | 11/2012 |
| GB | 2 520 779 A | 6/2015 |
| GB | 2 547 549 A | 8/2017 |
| JP | S 49-124893 | 5/1976 |
| JP | 2015-536697 | 12/2015 |
| WO | WO 2005/079896 A1 | 9/2005 |
| WO | WO 2017/140599 A1 | 8/2017 |
| WO | WO 2018/233794 A1 | 12/2018 |

OTHER PUBLICATIONS

Lavorini et al., "The ADMIT series—issues in inhalation therapy. 6) Training tools for inhalation devices" Primary Care Respiratory Journal (2010) 19(4) 335-341].

International Preliminary Examination Report issued in International Application No. PCT/EP2017/053057, dated Aug. 21, 2018.

Japanese Office Action issued in counterpart JP application No. 2018-541176, dated Feb. 15, 2021 with English language translation thereof.

* cited by examiner

DEVICE WITH FLOW RATE INDICATOR

CROSS REFERENCE TO RELATED APPLICATIONS

The present application is a § 371 National Phase application based on PCT/EP2017/053059 filed Feb. 10, 2017, which claims the benefit of Great Britain application Nos. 1602639.5 filed Feb. 15, 2016 and 1700412.8 filed Jan. 10, 2017 the subject matter of each of which is incorporated by reference in their entirety.

FIELD OF THE INVENTION

The present invention relates to a device for indicating a predetermined fluid flow rate. In particular, the present invention relates to a device for indicating a predetermined air flow rate during inhalation and/or exhalation. For example, the present invention relates to drug delivery inhaler devices or devices for attachment to drug delivery inhaler devices, such as pressurised metered dose inhaler (pMDI) devices and dry powder inhaler (DPI) devices. The invention also relates to methods of operation of such devices.

BACKGROUND OF THE INVENTION

There are many devices such as respiratory inhalers (e.g. pressurised metered dose inhalers (pMDIs) and dry powder inhalers (DPIs)) for respiratory drug delivery, spacers/holding chambers for use with such respiratory inhalers and spirometers for measurement of lung volume and/or peak inspiratory/expiratory flow where it is desirable to provide an indication of a fluid (air) flow rate through the device to monitor and/or facilitate correct usage of the device.

GB-A-2372704 discloses a device for providing an indication of the respiratory flow rate of a patient. The device includes two reeds adapted to generate an audible signal at different air flow speeds through the device. The first reed generates an audible signal of a first pitch when the air flow reaches a predetermined minimum. The second reed generates an audible signal of a second pitch when the air flow reaches a predetermined maximum. Thus, the patient is informed when the air flow is within a desirable range, between the predetermined minimum and maximum.

Lavorini et al (2010) [F. Lavorini, M. L. Levy, C. Corrigan and G. Crompton, "The ADMIT series—issues in inhalation therapy. 6) Training tools for inhalation devices" Primary Care Respiratory Journal (2010) 19(4) 335-341] set out a review of training tools for inhalation devices, including the device disclosed in GB-A-2372704, referred to as the "2Tone" trainer.

Lavorini et al (2010) comment that two of the most critical patient errors in the uses of pMDI devices are a failure to coordinate inhalation with actuation of the device and inhaling the aerosolized drug too quickly. This is considered to be a critical issue—incorrect use of a pMDI device means that the drug delivered to the patient is being delivered sub-optimally. In turn, this means that the patient does not receive the correct dose of the drug, which can lead to serious problems in the ongoing treatment of conditions such as asthma.

GB-A-2490770 discloses a pMDI actuator body and a spacer for a pMDI inhaler that incorporates an air flow rate indicator comprising a reed which oscillates and generates a sound signal at a predetermined minimum level suitable for delivery of the drug to the patient.

There is a desire to provide an improved air flow rate indicator for such devices (e.g. respiratory inhalers including pMDIs and DPIs, spacer/holding chambers for such inhalers, and spirometers) that has a simple construction thus facilitating manufacture and reducing manufacturing costs.

There is also a desire for a system/method that monitors a patient's usage of such a device (e.g. a respiratory inhaler) and, in particular, records air flow rates at the point of actuation of the device and the duration of the optimal flow rate for drug delivery after actuation.

Use of face masks by young children and the elderly is common to facilitate use of respiratory inhalers. Acceptance of and correct breathing through such face masks, especially by children can be difficult to achieve. Accordingly, there is a desire to provide a device for providing an indication of correct fitting and breathing technique for such face masks.

SUMMARY OF THE INVENTION

In a first aspect, the present invention provides a device for indicating a predetermined fluid flow rate, the device comprising:
  an aperture;
  a mouthpiece; and
  a body defining a fluid flow path extending between the aperture and the mouthpiece, the body comprising a fluid flow rate indicator operable to generate a sound signal to indicate when the fluid flow rate along the fluid flow path is at the predetermined fluid flow rate,
  wherein the fluid flow rate indicator comprises a corrugated portion having at least one corrugation extending into the fluid flow path.

The inventors have found that providing a fluid flow rate indicator comprising a corrugated portion having at least one and preferably a plurality of corrugations extending into the fluid flow path induces turbulent flow in a fluid moving along the fluid flow path when the fluid flow rate is above the predetermined rate. The turbulent flow produced generates the sound signal which can provide an indication that the predetermined flow rate has been achieved.

Without wishing to be bound to any theory, the inventors believe that the body allows laminar flow of fluid (e.g. gas/air) along the fluid flow path between the aperture and the mouthpiece at fluid flow rates below the predetermined fluid flow rate. As the fluid flow rate increases, the peak(s) and trough(s) of the corrugated portion induce turbulent eddies in the fluid until, at the predetermined fluid flow rate, sound oscillations are generated which match the resonant frequency of the corrugated portion of the body and thus generate a sound signal (which may or may not be audible to the human ear). The sound signal has a narrow frequency and detection of this frequency sound signal (either by the human ear and/or through software for audible sound signals, or through software for non-audible sound signals) can provide a clear indication of when the predetermined fluid flow rate has been achieved along the fluid flow path.

Optional features of the invention will now be set out. These are applicable singly or in any combination with any aspect of the invention.

In some embodiments, the body may define a fluid flow path having a substantially tubular (e.g. cylindrical) portion. For example, the body may comprise a substantially tubular (e.g. cylindrical) portion defining the substantially tubular (e.g. cylindrical) fluid flow path portion and/or the body may comprise a substantially tubular (e.g. cylindrical) channel defining the substantially tubular (e.g. cylindrical) fluid flow path portion. The cross sectional profile of the tubular flow path portion/tubular body portion/tubular channel may be substantially circular, oval or barrel-shaped.

The corrugated portion may form at least part of an inner wall of the body e.g. it may form at least part of (or even the whole of) the body/tubular body portion and/or at least part of the inner wall of the tubular channel. The corrugated portion may be integrally formed as part of the body e.g. it may be integrally formed with the tubular body portion/walls of the tubular channel. For example, the corrugation(s) may be formed (e.g. moulded) on an interior surface of the body/tubular body portion/tubular channel. By providing a corrugated fluid flow rate indicator integrally formed with the body, e.g. formed/moulded on an interior surface, the device has a simple construction with minimal components and no moving parts.

Alternatively, the corrugated portion may be separately formed and inserted into the body e.g. as an inner sleeve at least partially lining the interior surface of the body/tubular body portion/channel or as a strip affixed to the interior surface of the body/tubular body portion/channel.

In some embodiments, the tubular body portion is substantially cylindrical with the corrugated portion provided within an axially oriented recess (extending parallel to the fluid flow path) provided in the tubular body portion.

The inner walls of the channel/inner surface of the body may be substantially smooth (uncorrugated) in areas other than in the corrugated portion. For example, the tubular body portion may have smooth (un-corrugated) inner surface with the corrugated portion provided within the axially oriented recess.

The body and/or the corrugated portion may be substantially rigid, unlike the known rubbery, flexible corrugated breathing hoses.

In some embodiments, the corrugated portion may completely encircle the fluid flow path. In other embodiments, the corrugated portion may only partially surround the fluid flow path.

In some embodiments, the corrugated portion may extend the entire axial length of the body. In other embodiments, the corrugated portion may extend along a portion of the axial length of the body.

In some embodiments, the corrugated portion may have an axial length (extending parallel to the axis of the fluid flow path) of between 2 and 300 mm. The corrugated portion may have an axial length between 6 and 70 mm (such as between 6 and 15 mm in some examples) or between 10 and 70 mm, such as between 20 and 50 mm, for example around 33-36 mm in some examples.

In some embodiments, the tubular body portion/channel has an internal diameter of between 2 and 8 mm e.g. between 3 and 7 mm and preferably around 5 mm. In other embodiments, the tubular body/channel may have a larger internal diameter (e.g. between 24-28 mm) but will, when used, have an occlusion such that the air flow path is restricted. The occlusion may, for example, be a drug reservoir housed in the tubular body/channel.

In some embodiments, the resistance of the tubular body portion/channel is between 0.3 and 3.6 kPa at a flow rate of 30 L/min and between 1.7 and 18.5 kPa at a flow rate of 60 L/min.

The inventors have found that use of a relatively short length of corrugation (e.g. a single corrugation or up to 3 or 10 corrugations) in a relatively narrow or restricted air flow path allows the generation of a single frequency sound signal at an air flow rate associated with human breathing (both inhalation and exhalation). Accordingly, the device can be used as an inhalation/exhalation device to indicate a predetermined air flow rate during inhalation/exhalation. Furthermore, using a relatively short length of corrugated portion in a relatively narrow gauge body allows the device to be of a size that can be easily hand-held.

The corrugated portion may comprise a plurality of parallel ridges/peaks spaced by a plurality of troughs/furrows which at least partially encircle the fluid flow path (and which may be formed into the inner surface of the body portion/walls of the channel).

The plurality of ridges/troughs (or the single ridge/trough for the single corrugation) may be oriented substantially perpendicularly to the fluid flow path or they/it may be at an angle to the fluid flow path.

In other embodiments, the corrugated portion comprises at least one spiral or screw-thread ridge/peak which encircles the fluid flow path (and which may be formed on the interior surface of the body/walls of the channel).

In some embodiments, the corrugated portion comprises between 1 and 170 corrugations. It may comprise between 1 and 150 corrugations, such as 1 and 100 corrugations, for example between 1 and 75 corrugations or between 1 and 50 corrugations or between 1 and 20 corrugations such as between 1 and 12 corrugations, or between 3 and 12 corrugations or between 7 and 12 corrugations, for example around 9 corrugations (i.e. 9 peaks/ridges and associated troughs/furrows) or around 3 corrugations (i.e. 3 peaks/ridges and associated troughs/furrows).

The pitch of the corrugations i.e. the spacing between adjacent peaks may be between 2-5 mm e.g. around 3 mm.

The height of the corrugation(s) i.e. the height from the base of a trough to the apex of the peak may be between 0.5 and 2.0 mm, for example between 0.5 and 1.0 mm e.g. around 0.6 mm.

In some embodiments, the or each ridge in the corrugated portion has an unsymmetrical longitudinal cross-sectional profile (i.e. the cross-sectional profile parallel to the direction of fluid flow). For example, the or each ridge may have a substantially sawtooth/shark fin profile with differing gradients on opposing (upstream/downstream) sides. The apex of the or each ridge is preferably rounded.

By providing an asymmetrical ridge, the device can be used to produce a first sound signal when fluid flows from the aperture to the mouthpiece (e.g. during inhalation) and a second sound signal when fluid flows from the mouthpiece to the aperture (e.g. during exhalation). The first and second sound signals could have different frequencies. In this way, two different sound signals could be generated, one at the predetermined flow rate along the flow path from the aperture to the mouthpiece and one at the (same) second predetermined flow rate along the flow path from the mouthpiece to the aperture. In other embodiments, the first and second sound signals may have the same frequency. In this way, the first sound signal could be generated at the predetermined flow rate along the flow path from the aperture to the mouthpiece and the second sound signal could be generated at a (different) second predetermined flow rate along the flow path from the mouthpiece to the aperture.

In some embodiments, the corrugated portion extends to the aperture. In other embodiments, the corrugated portion is spaced from the aperture.

In preferred embodiments, the corrugated portion comprises a lead-in portion at its axial end the lead-in portion comprising the or one of the ridges such that as fluid first enters the corrugated portion it enters on a "rising-slope" and is directed towards the axis of the body/channel by the inclined surface of the or one of the ridges.

Some embodiments comprise a plurality of corrugated portions as described above. The corrugated portions may be axially spaced along the tubular body portion/channel with the un-corrugated e.g. smooth inner surface of the tubular body portion/channel interposed between the corrugated portions. Alternatively, they may be circumferentially spaced around the tubular body portion/channel.

In some embodiments, the body may have a substantially smooth outer surface (opposing the inner surface which defines the fluid flow path). In other embodiments, the body may have a corrugated outer surface (e.g. opposing the corrugated portion in the fluid flow path) for providing a visual and tactile distinction to users over known devices without the corrugated flow rate indicator.

In some embodiments, the corrugated portion may comprise an axially extendable wall portion of the body, e.g. the corrugated portion may form a bellows/concertina portion in the body wall. In these embodiments the axial extension of the corrugated portion may be varied to vary the frequency/pitch of the sound signal generated. For example, in a first position with the bellows/concertina wall portion extended, the sound signal will have a first frequency/pitch associated with a first predetermined flow rate and in a second position with the bellows/concertina portion compressed, the sound signal will have a second frequency/pitch associated with a second predetermined flow rate.

In some embodiments, the present invention provides a patient inhalation/exhalation device comprising:
 at least one aperture for inlet or outlet of air into/from the device;
 a mouthpiece for communication with the mouth of the patient;
 a body defining an air flow path extending between the aperture and the mouthpiece along which air is drawn to the mouthpiece by inhalation by the patient or air is forced towards the aperture by exhalation by the patient, the body comprising an air flow rate indicator operable to generate a sound signal to indicate when the air flow rate along the air flow path is at or above a predetermined minimum level,
 wherein the air flow rate indicator comprises a corrugated portion having at least one corrugation extending into the fluid flow path.

The corrugated portion and body may be as described above and there may be a plurality of corrugated portions.

The device is preferably adapted such that the sound signal is generated at an air flow rate of between 30 and 800 L/min.

In some embodiments, the device is a spirometer for measuring lung volume and/or peak flow of a patient. Such a spirometer has no moving parts which complicate manufacture and which may wear out. Furthermore, such a spirometer would not require periodic calibration.

In these embodiments, the corrugated portion may have an axial length (extending parallel to the axis of the fluid flow path) of between 100 and 300 mm. Such a corrugated portion may have between 100 and 170 corrugations i.e. peaks/troughs.

The inventors have found that using a corrugated portion having this axial length results in a sound signal that switches from frequency to frequency and is substantially continuous as the air flow rate changes. At shorter lengths, the sound signal is not continuous and only sounds at the predetermined flow rate(s). The continuous sound generated by the corrugated portion can be used to monitor correct usage of the spirometer. Additionally/alternatively, the lung volume can be derived from calculations using the duration of the exhalation and the flow rate (derived from the frequency of the sound signal).

In the spirometer, the mouthpiece and the body may be substantially co-axial. The mouthpiece and body may be substantially tubular e.g. cylindrical.

The spirometer device is preferably adapted such that the sound signal is generated at an air flow rate of between 50 and 800 L/min.

In some embodiments, the device is a respiratory inhaler device adapted to deliver respiratory drugs to a user. In these inhaler devices, the predetermined flow rate may be the minimum air flow rate for optimal drug inhalation (e.g. 30-60 L/min). In this way, the generation and detection of the sound signal provides an indication to the user that actuation of the inhaler device can be effected to deliver the drug into the air flow path or that the inspiratory breath is of an appropriate flow rate to deliver drug from a primed inhaler (e.g. a dry powder drug).

Accordingly, in a preferred embodiment, the present invention provides a respiratory inhaler device for delivery of a drug to a patient, the device comprising:
 an aperture for inlet of air into the device;
 a mouthpiece for communication with the mouth of a patient;
 a body defining an air flow path extending from the aperture to the mouthpiece along which air is drawn to the mouthpiece by inhalation by the patient, the body comprising an air flow rate indicator operable to generate a sound signal to indicate when the air flow rate along the air flow path is at or above a predetermined minimum level suitable for delivery of the drug to the patient,
 wherein the air flow rate indicator comprises a corrugated portion having at least one corrugation extending into the air flow path.

The corrugated portion and body may be as described above and there may be a plurality of corrugated portions.

In some embodiments, the corrugated portion in the inhaler device may have an axial length (extending parallel to the axis of the air flow path) of between 6 and 70 mm (such as between 6 and 15 mm in some examples) or between 20 and 50 mm, for example around 33-36 mm for some examples.

The inventors have found that providing a corrugated portion having an axial length of at least 30 mm can provide a device that generates two (or more) sound signals (of differing frequencies) within an air flow rate range associated with human inhalation (e.g. in the range of 20-60 l/min). This can be used, for example, to indicate the range of air flow rates suitable for optimal drug delivery with the first sound signal being generated at the predetermined minimum level and a second sound signal being generated at a predetermined maximum level.

In these embodiments, the inhaler device preferably further comprises a seat for location of a drug reservoir, the drug reservoir being operable to deliver a dose of drug into the air flow path for inhalation by the patient. The corrugated portion is preferably provided upstream (i.e. closer to the inlet aperture) than the seat for location of the drug reservoir. The term "drug reservoir" may mean either a multiple dose reservoir (e.g. a canister) a single unit dose reservoir (e.g. a blister or capsule) and/or a multi-unit dose reservoir (e.g. a strip of blisters). Other types of reservoir are included.

In some embodiments, the inhaler device may be a pressurised metered dose inhaler (pMDI) device. In such devices, the drug (or combination of drugs) is typically provided in the form of a liquid in solution or suspension held in a pressurised canister. Actuation of the canister is typically achieved by depressing the canister downwards into the body of the device. This causes an interaction between the canister and the seat that causes a metered dose of liquid to be ejected from the canister, along with a propellant gas. In this manner, the liquid is aerosolized for inhalation by the patient.

Pressurised metered dose inhaler (pMDI) devices typically have a body comprising an upright portion extending from an aperture to a transverse mouthpiece for communication with the mouth of the patient. As well as allowing the inlet of air into the device, the aperture is adapted to receive the drug reservoir (canister) which is housed in the upright portion thus partially occluding the air flow path. The seat for the location of the drug reservoir (canister) is typically provided at the junction between the upright portion and the transverse mouthpiece.

In these embodiments the corrugated portion is preferably provided in or is integrally formed with at least part of the upright body portion which, in use, houses the canister such that the corrugated portion at least partially surrounds the canister in use.

The upright portion is typically tubular (e.g. cylindrical). It may have a circular cross section. In some embodiments, it may have an oval or barrel-shaped cross section. It may have an internal diameter of 24-28 mm. In preferred embodiments, the tubular upright portion is substantially cylindrical and dimensioned such that a drug canister forms a snug fit against the inner wall of the upright portion with the corrugated portion provided within an axially oriented recess (extending parallel to the air flow path) provided in the upright portion. This ensures that the air drawn along the air flow path by inhalation passes over the corrugated portion.

In these embodiments, the or each corrugated portion may have between 7 and 10 peaks/troughs.

To use the pMDI, the patient will insert the mouthpiece into their mouth and inhale. The air flowing into the upright portion of the body through the aperture will flow over the corrugated portion and into the transverse mouthpiece towards the patient's mouth. At the predetermined minimum flow rate, the air drawn along the air flow path will become turbulent as a result of the air tumbling over the peaks and troughs of the corrugated portion. When the oscillations match the resonant frequency of the corrugated portion of the body, a sound signal having a narrow frequency width will be generated and the patient will know that the optimal inhalation rate has been achieved. The patient will then know to actuate/depress the drug canister to release the drug into the air flow path for inhalation.

The generation of the sound signal may be detected by ear by the patient or the patient may be provided with software (e.g. in the form of a mobile phone app) to detect the generation of the sound signal and thus the attainment of the predetermined minimum flow rate for optimal drug delivery.

Upon depression of the canister, the frequency/pitch of the sound signal may change as a result of the change in the resistance along the air flow path if the axial length of the corrugated portion opposed to the canister changes (e.g. increases). In situations where there is a desire to monitor patient compliance, the alteration in the frequency/pitch of the sound signal could be monitored/recorded (e.g. by the computer software/mobile app) to detect the point of actuation of the canister. This would provide a cheap and easy-to-use method for monitoring patient usage which could capture not only the number of actuations but also record flow rates associated with actuations and the duration of the optimal air flow rate after actuation.

In some embodiments, the inhaler device may be a dry powder inhaler (DPI) device. For example, it may be a Monodose™, Clickhaler™, Turbohaler™ or Aerolizer™ DPI device. In such devices, the drug is typically provided in the form of a powder that is released from a doseable reservoir, capsule or blister into the air flow path upon actuation by the patient. Conventionally, DPIs are primed (i.e. drug released from reservoir, blister pierced etc.) with the drug then being aerosolised via the action of inhalation. Thus they may be termed "breath-actuated inhalers". Incorrect respiratory effort by the patient leads to delivery of an incorrect dosage and/or incomplete de-aggregation of the powder.

DPI inhalers typically have an air flow path defined by a body having a channel (e.g. a tubular channel) extending from the aperture/air inlet to a mouthpiece for communication with the mouth of the patient via the seat for the location of the drug reservoir.

In some embodiments, the mouthpiece may be transverse/perpendicularly disposed relative to the channel. In other embodiments, the mouthpiece may be substantially axially aligned with the channel.

In such inhalers, the corrugated portion may be provided in the channel proximal the aperture providing for inlet of air into the device.

A second aperture defining a second air inlet for the device may be provided. The first and second apertures may be provided on opposing lateral sides of the body such that the body defines two opposing channels (e.g. two tubular channels) that join proximal the mouthpiece. The two channels and the mouthpiece may form a substantially T-shaped air flow path through the device where the mouthpiece is transverse to the channel.

In such inhalers, a second corrugated portion may be provided in the second tubular channel proximal the second aperture.

In some embodiments, the two corrugated portions may have different axial lengths and/or ridges/troughs of differing pitch/height such that the sound signals generated by each corrugated portion differ in frequency.

To use the DPI, the patient will prime the inhaler, insert the mouthpiece into their mouth and inhale. The air flowing into the device through the aperture(s) will flow over the corrugated portion(s) and towards the mouthpiece. At the predetermined minimum flow rate, the air drawn along the air flow path will become turbulent as a result of the air tumbling over the peaks and troughs of the corrugated portion(s). When the oscillations match the resonant frequency of the corrugated portion or the body, a sound signal having a narrow frequency width will be generated and the patient will know that the optimal inhalation rate has been achieved and that they are inhaling correctly.

The generation of the sound signal may be detected by ear by the patient or the patient may be provided with software (e.g. in the form of a mobile phone app) to detect the generation of the sound signal and thus the attainment of the predetermined minimum flow rate for optimal drug delivery. The FrequenSee™ app available as an Apple® and Android® app may, for example, be used for detecting the generation of the sound signal.

In another embodiment, the present invention provides a spacer or holding chamber for a respiratory inhaler for delivery of a drug to a patient, the spacer/holding chamber comprising:

an aperture for inlet of air into the spacer/holding chamber, the aperture being adapted to receive a mouthpiece of the respiratory inhaler;

a mouthpiece for communication with the mouth of a patient;

a body defining an air flow path extending from the aperture to the mouthpiece along which air is drawn to the mouthpiece by inhalation by the patient, the body comprising an air flow rate indicator operable to generate a sound signal to indicate when the air flow rate along the air flow path is at or above a predetermined minimum level suitable for delivery of the drug to the patient, wherein the air flow rate indicator comprises a corrugated portion having at least one corrugation extending into the fluid flow path.

The corrugated portion and body may be as described above and there may be a plurality of corrugated portions.

In preferred embodiments, the body is a substantially tubular body e.g. having a barrel-shaped cross-sectional profile. The mouthpiece may be provided as an aperture at an opposing lateral end of the body to the aperture for inlet of air into the device.

The corrugated portion may be provided integrally with the tubular body e.g. formed/moulded onto the interior surface of the tubular body. It may be provided in an axially oriented recess provided on the interior surface of the body.

In some embodiments, the holding chamber includes a valve proximal the mouthpiece. For example, the holding chamber may be valved holding chamber such as known as the Able Spacer™ or A2A Spacer™. In these embodiments, the corrugated portion is provided between the valve and the mouthpiece.

In another preferred embodiment, the present invention provides a face mask testing device for monitoring fit and use of a face mask, the device comprising:

a mouthpiece for communication with the mouth of a patient, the mouthpiece defined by a mask portion, a body defining an air flow path extending from a body aperture to the mouthpiece along which air is drawn to the mouthpiece by inhalation by the patient, the body comprising an air flow rate indicator operable to generate a sound signal to indicate when the air flow rate along the air flow path is at or above a predetermined minimum level, wherein the air flow rate indicator comprises a corrugated portion having at least one corrugation extending into the air flow path; and an adapter mounted on the mask portion and comprising an adapter aperture for selectively receiving a spacer/mouthpiece of a pMDI or the body.

The face mask testing device can be used to increase acceptance, to check the fit of and to ensure correct breathing through the mask portion by the user e.g. a child or elderly person. The generation of the sound signal will only occur if the mask is correctly fitted and the breathing technique is correct. The sound signal can incentivise a young user to accept and use the face mask portion. In a second aspect, the present invention provides a system comprising a device according to the first aspect and a sound receiver for detecting the sound signal.

In some embodiments, the sound receiver comprises computer software e.g. an application for running on a mobile device such as a smartphone app. The FrequenSee™ app, available as an Apple® and Android® app, may be used for detecting the sound signal.

In a third aspect, the present invention provides a method of monitoring actuation of a respiratory inhaler device for delivery of a drug to a patient, the method comprising:

providing a system according to the second aspect, detecting the sound signal generated when the air flow rate along the air flow path is at or above the predetermined minimum level suitable for delivery of the drug to the patient, detecting a change in frequency of the sound signal upon actuation of the device by the patient.

In some embodiments, the method comprises recording (e.g. using computer software such as an application for running on a mobile device such as a smartphone app) the duration of the change in the sound signal upon actuation by detecting the return to the original sound signal after actuation is complete.

In some embodiments, the method comprises recording (e.g. using computer software such as an application for running on a mobile device such as a smartphone app) the duration of the sound signal (e.g. the duration after actuation) to establish the duration of optimal inhalation by the patient.

This information can be used to monitor use of the inhaler by the patient. It can be used (either by the patient or by a healthcare provider) to ensure that actuation is being correctly coordinated with the optimal air flow rate through the device and that the optimal air flow rate is being maintained for a sufficient period of time after actuation. Current monitoring methods typically only monitor the number of actuations of the inhaler device and do not provide any information about the air flow rate at the time of actuation nor about the correct inhalation technique after actuation.

In a fourth aspect, the present invention provides a device for indicating a desired fluid flow rate along a fluid flow path through a respiratory inhaler, the device comprising:

an inlet aperture;

an outlet aperture for fluid communication with the fluid flow path through the respiratory inhaler; and a body defining a second fluid flow path extending between the inlet aperture and the outlet aperture, the body comprising:

a connector portion for connection to the respiratory inhaler; and a fluid flow rate indicator operable to generate a sound signal to indicate when the fluid flow rate along the second fluid flow path is at a predetermined fluid flow rate, wherein the fluid flow rate indicator comprises a corrugated portion having at least one corrugation extending into the second fluid flow path.

The inventors have found that providing a fluid flow rate indicator comprising a corrugated portion having at least one and preferably a plurality of corrugations extending into the second fluid flow path induces turbulent flow in a fluid moving along the second fluid flow path when the fluid flow rate is above the predetermined rate. The turbulent flow produced generates the sound signal which can provide an indication that the predetermined flow rate has been achieved.

Without wishing to be bound to any theory, the inventors believe that the body allows laminar flow of fluid (e.g. gas/air) along the second fluid flow path between the inlet aperture and the outlet aperture at fluid flow rates below the predetermined fluid flow rate. As the fluid flow rate increases, the peak(s) and trough(s) of the corrugated portion induce turbulent eddies in the fluid until, at the predetermined fluid flow rate, sound oscillations are generated which match the resonant frequency of the corrugated portion of the body and thus generate a sound signal (which may or may not be audible to the human ear). The sound signal has a narrow frequency and detection of this frequency sound signal (either by the human ear and/or through software for audible sound signals, or through software for non-audible sound signals) can provide a clear indication of when the predetermined fluid flow rate has been achieved along the second fluid flow path.

The predetermined flow rate is selected to be that at which the desired flow rate is achieved within the respiratory inhaler. For example, the predetermined flow rate may selected to be that at which the flow rate within the respiratory inhaler is the minimum air flow rate for optimal drug inhalation (e.g. 30-60 L/min). In this way, the generation and detection of the sound signal provides an indication to the user that actuation of the respiratory inhaler can be effected to deliver the drug into the inhaler air flow path or that the inspiratory breath is of an appropriate flow rate to deliver drug from a primed inhaler (e.g. a dry powder drug).

Optional features of the fourth aspect will now be set out.

In some embodiments, the body may define a second fluid flow path having a substantially tubular (e.g. cylindrical) portion. For example, the body may comprise a substantially tubular (e.g. cylindrical) portion defining the substantially tubular (e.g. cylindrical) second fluid flow path portion and/or the body may comprise a substantially tubular (e.g. cylindrical) channel defining the substantially tubular (e.g. cylindrical) second fluid flow path portion. The cross sectional profile of the tubular second fluid flow path portion/tubular body portion/tubular channel may be substantially circular, oval or barrel-shaped.

The corrugated portion may form at least part of an inner wall of the tubular body portion or tubular channel. The corrugated portion may be integrally formed as part of the body e.g. it may be integrally formed with the inner walls of the tubular body portion/tubular channel. For example, the corrugation(s) may be formed (e.g. moulded) on the inner walls of the tubular body/tubular channel. By providing a corrugated fluid flow rate indicator integrally formed with the body, the device has a simple construction with minimal components and no moving parts.

Alternatively, the corrugated portion may be separately formed and inserted into the body e.g. as an inner sleeve at least partially lining the interior surface of the body/tubular body portion/channel or as a strip affixed to the inner walls of the body/tubular body portion/channel.

The body and/or the corrugated portion may be substantially rigid, unlike the known rubbery, flexible corrugated breathing hoses.

The inner walls/inner surface of the body/tubular body portion/channel may be substantially smooth (uncorrugated) in areas other than in the corrugated portion.

In other embodiments, the corrugated portion may completely encircle the second fluid flow path. In other embodiments, the corrugated portion may only partially surround the second fluid flow path.

In some embodiments, the corrugated portion may extend substantially the entire length of the second fluid flow path. In other embodiments, the corrugated portion may extend along only a portion of the length of the second fluid flow path.

In some embodiments, the corrugated portion may have an axial length (extending parallel to the axis of the second fluid flow path) of between 6 and 70 mm (such as between 6 and 15 in some examples) or between 20 and 50 mm, for example around 33-36 mm in some examples.

The inventors have found that providing a corrugated portion having an axial length of at least 30 mm can provide a device that generates two (or more) sound signals (of differing frequencies) within an air flow rate range associated with human inhalation (e.g. in the range of 20-60 l/min). This can be used, for example, to indicate the range of air flow rates suitable for optimal drug delivery with the first sound signal being generated at a desired minimum level and a second sound signal being generated at a desired maximum level.

In some embodiments, the tubular body portion/channel has an internal diameter of between 2 and 8 mm e.g. between 3 and 7 mm and preferably around 5 mm.

In some embodiments, the resistance of the tubular body portion/channel is between 0.3 and 3.6 kPa at a flow rate of 30 L/min and between 1.7 and 18.5 kPa at a flow rate of 60 L/min.

The inventors have found that use of a relatively short length of corrugation in a relatively narrow or restricted air flow path allows the generation of a single frequency sound signal at an air flow rate associated with human breathing (both inhalation and exhalation). Accordingly, the device can be used to indicate a desired air flow rate through a respiratory inhaler during inhalation. Furthermore, using a relatively short length of corrugated portion in a relatively narrow gauge body/tubular body portion/channel allows the device to be of a size that can be easily hand-held.

The corrugated portion may comprise a plurality of parallel ridges/peaks spaced by a plurality of troughs/furrows which at least partially encircle the second fluid flow path (and which may be provided/formed on the inner walls of the body/tubular body portion/channel).

The plurality of ridges/troughs (or the single trough/ridge) may be oriented substantially perpendicularly to the second fluid flow path or they may be at an angle to the second fluid flow path.

In other embodiments, the corrugated portion comprises at least one spiral or screw-thread ridge/peak which encircles the second fluid flow path (and which may be provided/formed on the inner walls of the body/tubular body portion/channel).

In some embodiments, the corrugated portion comprises between 1 and 170 corrugations. It may comprise between 1 and 150 corrugations, such as 1 and 100 corrugations, for example between 1 and 75 corrugations or between 1 and 50 corrugations or between 1 and 20 corrugations such as between 1 and 12 corrugations, or between 3 and 12 corrugations or 7 and 12 corrugations, for example around 9 corrugations (i.e. 9 peaks/ridges and associated troughs/furrows) or around 3 corrugations (i.e. 3 peaks/ridges and associated troughs/furrows).

The pitch of the corrugations i.e. the spacing between adjacent peaks may be between 2-5 mm e.g. around 3 mm.

The height of the corrugation(s) i.e. the height from the base of a trough to the apex of the peak may be between 0.5 and 2.0 mm, for example between 0.5 and 1.0 mm e.g. around 0.6 mm.

Some embodiments comprise a plurality of corrugated portions as described above. The corrugated portions may be axially spaced along the tubular body portion/channel with the un-corrugated e.g. smooth inner surface of the tubular body portion/channel interposed between the corrugated portions. Alternatively, they may be circumferentially spaced around the tubular body portion/channel.

The inlet aperture may be an axial aperture i.e. aligned with the axis of the second fluid flow path. In some embodiments, the inlet aperture is defined by a funnel-shaped body portion/channel with the maximum diameter of the funnel provided distal the outlet aperture such that fluid (air) is funnelled into the second fluid (air) flow path.

The connector portion is provided to connect/fit the device to a respiratory inhaler. A respiratory inhaler typically comprises a tubular inhaler body portion The connector portion may have a recess within which the respiratory inhaler (e.g. the tubular inhaler body portion) may be received and retained e.g. by a friction fit. The recess may be a tubular recess. For example, the connector portion may be a full or partial tubular sleeve for at least partly encircling the tubular inhaler body portion. The tubular recess may have an axis extending parallel to the axis of the second fluid flow path. Accordingly, the second fluid flow path may have an axis extending parallel to the axis of the tubular inhaler body portion.

In some embodiments, the device is adapted for connection to a dry powder inhaler (DPI). In such inhalers, the drug is typically provided in the form of a powder that is released from a drug source e.g. doseable reservoir, capsule or blister, into the inhaler air flow path upon actuation by the patient. Conventionally, DPIs are primed (i.e. drug released from reservoir, blister pierced etc.) with the drug then being aerosolised via the action of inhalation.

Incorrect respiratory effort by the patient leads to delivery of an incorrect dosage and/or incomplete de-aggregation of the powder.

DPIs typically have an inhaler air flow path defined by an inhaler body having at least one inhalation channel extending from at least one air inlet to a mouthpiece for communication with the mouth of the patient via the seat for the location of the drug source.

DPIs (such as Astra Zeneca's Turbohaler™ or Teva's Spiromax™) may have a substantially tubular inhaler body portion having at least one radial air inlet (i.e. which is radial relative to the axis of the tubular inhaler body portion) and which is typically provided proximal the mouthpiece. In some DPIs (an example of which is Astra Zeneca's Turbohaler™), the at least one radial air inlet is provided in addition to a terminal inlet provided at or proximal an axial end of the inhaler body distal the mouthpiece.

Inhalation by the user draws air through the radial air inlet (and the terminal air inlet if present) to the mouthpiece of the DPI.

In some embodiments, the outlet aperture of the device may be a radial aperture i.e. radially aligned with the (longitudinal) axis of the second fluid flow path. In this way, it can provide fluid communication with the inhaler air flow path via the radial inlet of the respiratory inhaler.

The outlet aperture of the second fluid flow path may open into the recess of the connector portion where the connector portion is adapted to at least partially encircle the inhaler body in the location of the radial air inlet of the inhaler body portion.

The device may be adapted such that when fitted to the respiratory inhaler, the inlet aperture is located distal the inhaler mouthpiece e.g. the inlet aperture may be located adjacent the terminal air inlet (where present) or adjacent the axial end of the tubular inhaler body distal the mouthpiece.

Inhalation by the user draws air through the radial air inlet of the DPI via the inlet aperture and secondary flow path of the device (as well as through the terminal air inlet of the DPI if present). When the air flow rate along the second air flow path reaches a predetermined flow rate (which is obtained when a desired fluid flow rate along with inhaler air flow path is reached), the air flow over the corrugated portion in the second fluid flow path will become turbulent as a result of the air tumbling over the peak(s) and trough(s) of the corrugated portion(s). When the oscillations match the resonant frequency of the corrugated portion or the body, a sound signal having a narrow frequency width will be generated and the patient will know that the optimal inhalation rate has been achieved and that they are inhaling correctly.

In some embodiments, the device is adapted for connection to a pressurised metered dose inhaler (pMDI).

In such devices, the drug (or combination of drugs) is typically provided in the form of a liquid in solution or suspension held in a pressurised canister. Actuation of the canister is typically achieved by depressing the canister downwards into the body of the device. This causes an interaction between the canister and a seat that causes a metered dose of liquid to be ejected from the canister, along with a propellant gas. In this manner, the liquid is aerosolized for inhalation by the patient.

Pressurised metered dose inhaler (pMDI) devices typically have a body comprising an upright tubular inhaler body portion extending from an air inlet to a transverse mouthpiece for communication with the mouth of the patient. As well as allowing the inlet of air into the device, the inlet is adapted to receive the drug reservoir (canister) which is housed in the upright portion thus partially occluding the air flow path. The seat for the location of the drug reservoir (canister) is typically provided at the junction between the upright portion and the transverse mouthpiece.

In these embodiments, the tubular (e.g. cylindrical) body portion defining the second fluid flow path is dimensioned to extend within the upright portion of the pMDI inhaler body portion such that, in use, the outlet aperture is provided upstream of the valve seat for location of the drug canister (and thus upstream of the point at which the drug is aerosolised in the inhaler air flow path). The tubular body portion defining the second fluid flow path is aligned parallel to the inhaler air flow path in use.

In these embodiments, the connector portion may comprise a cap for seating on the upright portion of the pMDI body encircling the air inlet or a sleeve for encircling the upright portion of the pMDI body. The connector cap will have an aperture through which a drug reservoir/canister can be inserted into the upright portion. The connector cap may comprise an annular rim with a downwardly depending skirt, the skirt dimensioned to be inserted into and form an interference fit with the upright portion of the pMDI body.

The inlet aperture of the tubular (e.g. cylindrical) body portion defining the second air flow path is provided such that it is spaced from and above the annular rim/sleeve. Therefore, in use, it is spaced from and above the air inlet of the upright portion of the pMDI body. This prevents impedance of the inlet aperture by the drug canister.

The connector cap may comprise a tab upstanding from the annular rim and the tubular body portion defining the second air flow path may be attached to or provided integrally with the upstanding tab such that the inlet aperture is above the annular rim.

The connector cap may further comprise a clip for connection to the substantially tubular portion of the body defining the second fluid flow path. The clip may be provided on the upstanding tab.

The outlet aperture of the second fluid flow path opens into the upright portion of the pMDI body (upstream of the seat for location of the drug reservoir) and thus is in fluid communication with the inhaler air flow path.

Inhalation by the user draws air through the air inlet of the pMDI (between the annular rim and the drug canister) and through the inlet aperture of the tubular body portion defining the second fluid flow path of the device. When the air flow rate along the second fluid flow path reaches a predetermined flow rate (which is obtained when a desired fluid flow rate along with inhaler air flow path is reached), the air flow over the corrugated portion in the second fluid flow path will become turbulent as a result of the air tumbling over the peaks and troughs of the corrugated portion(s). When the oscillations match the resonant frequency of the corrugated portion or the body, a sound signal having a narrow frequency width will be generated and the patient will know that the optimal inhalation rate has been achieved and that they are inhaling correctly.

In any embodiment of the fourth aspect, the body may define a further second fluid flow path extending between a further inlet aperture and a further outlet aperture, and a further fluid flow rate indicator operable to generate a further sound signal to indicate when the fluid flow rate along the further second fluid flow path is at a second predetermined fluid flow rate, wherein the further fluid flow rate indicator comprises a further corrugated portion having at least one corrugation extending into the further second fluid flow path.

By providing two flow rate indicators each having a different flow resistance (achieved by providing a different number of corrugations and/or by providing two second fluid flow paths having different path lengths/different cross sectional areas), it is possible to effect generation of two distinct signals which can be used to provide an audible indication of when two different predetermined fluid flow rates are achieved through the respiratory inhaler.

In other embodiments, two flow rate indicators may have the same number of corrugation(s) and/or the tubular bodies may have the same path length/same diameter so that the sound signal generated is amplified.

The further second fluid flow path, further inlet aperture and further outlet aperture may be as described above for the second fluid flow path, inlet aperture and outlet aperture.

For example, the body may comprise a further substantially tubular (e.g. cylindrical) portion defining the further substantially tubular (e.g. cylindrical) second fluid flow path portion and/or the body may comprise a further substantially tubular (e.g. cylindrical) channel defining the further substantially tubular (e.g. cylindrical) second fluid flow path portion. The cross sectional profile of the further tubular second fluid flow path portion/tubular body portion/tubular channel may be substantially circular, oval or barrel-shaped.

The further inlet and outlet apertures may both be provided upstream of the seat for location of the drug reservoir.

The further corrugated portion may be as described above for the corrugated portion.

The further corrugated portion forming the further flow rate indicator may form at least part of an inner wall of the further tubular body portion or tubular channel. The further corrugated portion may be integrally formed as part of the body e.g. it may be integrally formed with the inner walls of the further tubular body portion/tubular channel. For example, the corrugation(s) may be formed (e.g. moulded) on the inner walls of the further tubular body portion/tubular channel.

Alternatively, the further corrugated portion may be separately formed and inserted into the body e.g. as an inner sleeve at least partially lining the interior surface of the further tubular body portion/channel or as a strip affixed to the inner walls of the further tubular body portion/channel.

The further tubular body portion/channel may have a different length and/or a different internal diameter in order to generate a different flow resistance in the further tubular body than in the tubular body portion/channel.

The inner walls/inner surface of the further tubular body portion/channel may be substantially smooth (uncorrugated) in areas other than in the further corrugated portion.

In other embodiments, the further corrugated portion may completely encircle the further second fluid flow path. In other embodiments, the further corrugated portion may only partially surround the further second fluid flow path.

In some embodiments, the further corrugated portion may extend substantially the entire length of the further second fluid flow path. In other embodiments, the further corrugated portion may extend along only a portion of the length of the further second fluid flow path.

In some embodiments, the further corrugated portion may have an axial length (extending parallel to the axis of the second fluid flow path) of between 6 and 70 mm (such as between 6 and 15 mm in some embodiments) or between 20 and 50 mm, for example around 33-36 mm in some embodiments.

In some embodiments, the further tubular body portion/channel has an internal diameter of between 2 and 8 mm e.g. between 3 and 7 mm and preferably around 5 mm. The further tubular body portion/channel may have a different internal diameter than the tubular body portion/channel.

The further tubular body portion/channel may have a different axial length to the tubular body portion/channel.

In some embodiments, the resistance of the further tubular body portion/channel is between 0.3 and 3.6 kPa at a flow rate of 30 L/min and between 1.7 and 18.5 kPa at a flow rate of 60 L/min. Preferably, the resistance of the further tubular body portion/channel is different from the resistance of the tubular body portion/channel.

The further corrugated portion comprises at least one ridge/peak and at least one trough/furrow which at least partially encircle the further second fluid flow path (and which may be provided/formed on the inner walls of the further tubular body portion/channel).

The ridge(s)/trough(s) may be oriented substantially perpendicularly to the further second fluid flow path or they may be at an angle to the further second fluid flow path.

In other embodiments, the further corrugated portion comprises at least one spiral or screw-thread ridge/peak which encircles the further second fluid flow path (and which may be provided/formed on the inner walls of the further tubular body portion/channel).

In some embodiments, the further corrugated portion comprises between 1 and 170 corrugations. It may comprise between 1 and 150 corrugations, such as 1 and 100 corrugations, for example between 1 and 75 corrugations or between 1 and 50 corrugations or between 1 and 20 corrugations such as between 1 and 12 corrugations, or between 3 and 12 corrugations or between 7 and 12 corrugations, for example around 9 corrugations (i.e. 9 peaks/ridges and associated troughs/furrows) or around 3 corrugations (i.e. 3 peaks/ridges and associated troughs/furrows).

Where there is more than one corrugation in the further corrugated portion, the pitch of the corrugations i.e. the spacing between adjacent peaks may be between 2-5 mm e.g. around 3 mm.

The height of the corrugation(s) i.e. the height from the base of a trough to the apex of the peak may be between 0.5 and 2.0 mm, for example between 0.5 and 1.0 mm e.g. around 0.6 mm.

The corrugated portion may extend to the inlet aperture. The connector cap for the pMDI inhaler may comprise a further clip e.g. on the upstanding tap for securing the further tubular body portion defining the further second air flow path.

In a preferred embodiment of the fourth aspect, the present invention provides a device for indicating a desired fluid flow rate along a fluid flow path through a respiratory inhaler, the device comprising:
- a tubular body portion defining a second fluid flow path extending between an inlet aperture and an outlet aperture, the outlet aperture being for fluid communication with the fluid flow path through the respiratory inhaler;
- a connector portion for securing the tubular body portion to the respiratory inhaler; and
- a fluid flow rate indicator operable to generate a sound signal to indicate when the fluid flow rate along the second fluid flow path is at a predetermined fluid flow rate, wherein the fluid flow rate indicator comprises a corrugated portion having at least one corrugation extending into the second fluid flow path.

The tubular body portion, inlet aperture, outlet aperture, connector portion and corrugated portion are as described above. A plurality of corrugated portions may be provided as discussed above.

The device may comprise a further tubular body portion defining a further second fluid flow path extending between a further inlet aperture and a further outlet aperture, and a further fluid flow rate indicator operable to generate a further sound signal to indicate when the fluid flow rate along the further second fluid flow path is at a second predetermined fluid flow rate, wherein the fluid flow rate indicator comprises a further corrugated portion having at least one corrugation extending into the further second fluid flow path.

The further tubular body portion, further inlet aperture, further outlet aperture, and further corrugated portion are as described above. A plurality of further corrugated portions may be provided as discussed above.

The further tubular body portion, further inlet aperture and further outlet aperture may be as described above for the second fluid flow path, inlet aperture and outlet aperture.

For example, the further tubular body portion may be substantially cylindrical with a circular, oval or barrel-shaped transverse cross-section.

The connector cap for the pMDI inhaler may comprise a further clip e.g. on the upstanding tap for (optionally releasably) securing the further tubular body portion defining the further second air flow path within the inhaler air flow path.

The generation of the sound signal(s) may be detected by ear by the patient or the patient may be provided with software (e.g. in the form of a mobile phone app) to detect the generation of the sound signal and thus the attainment of the predetermined minimum flow rate for optimal drug delivery. The FrequenSee™ app available as an Apple® and Android® app may, for example, be used for detecting the generation of the sound signal.

In a fifth aspect, the present invention provides a method of monitoring actuation of a respiratory inhaler for delivery of a drug to a patient, the method comprising:
- providing a device according to the fourth aspect;
- fitting the device to the respiratory inhaler;
- detecting the sound signal generated when the air flow rate along the second air flow path is at or above the predetermined minimum; and
- detecting a change in frequency of the sound signal upon actuation of the device by the patient.

In some embodiments, the method comprises recording (e.g. using computer software such as an application for running on a mobile device such as a smartphone app) the duration of the change in the sound signal upon actuation by detecting the return to the original sound signal after actuation is complete.

In some embodiments where the device comprises a further flow rate indicator, the method further comprises detecting the sound signal generated when the air flow rate along the further second air flow path is at a predetermined maximum flow rate for optimal drug inhalation.

In some embodiments, the method comprises recording (e.g. using computer software such as an application for running on a mobile device such as a smartphone app) the duration of the sound signal (e.g. the duration after actuation) to establish the duration of optimal inhalation by the patient.

This information can be used to monitor use of the inhaler by the patient. It can be used (either by the patient or by a healthcare provider) to ensure that actuation is being correctly coordinated with the optimal air flow rate through the device and that the optimal air flow rate is being maintained for a sufficient period of time after actuation. Current monitoring methods typically only monitor the number of actuations of the inhaler device and do not provide any information about the air flow rate at the time of actuation nor about the correct inhalation technique after actuation.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Figure 1:
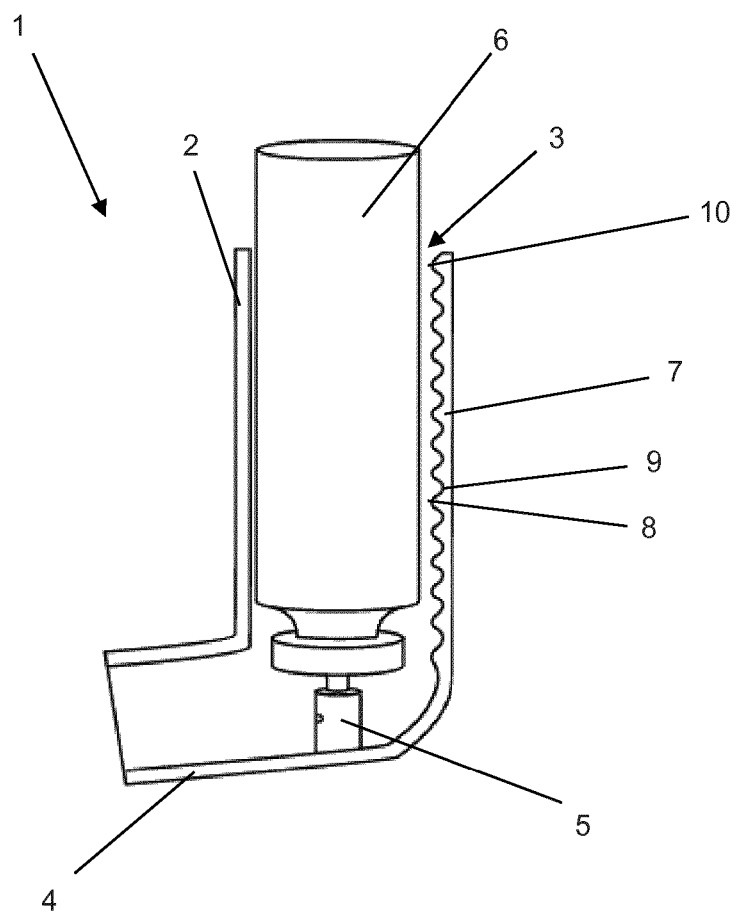
FIG. 1 shows a longitudinal cross-sectional view through a first embodiment of the present invention.

FIG. 1 shows a longitudinal cross-sectional view through a first embodiment of the present invention which comprises a pressurised metered dose inhaler (pMDI) 1 adapted to deliver respiratory drugs to a patient. The body of the pMDI 1 comprises an upright portion 2 having an aperture 3 for inlet of air into the pMDI and a transverse mouthpiece 4 for communication with the mouth of a patient. The upright portion 2 defines an air flow path extending from the aperture 3 to the transverse mouthpiece 4. The upright portion 2 is substantially cylindrical (with a substantially circular transverse cross-section) and the transverse mouthpiece 4 has a substantially oval or barrel-shaped transverse cross-section. This provides an oval or barrel-shaped mouthpiece 4 that can easily form a seal with the patient's mouth.

The upright portion has an internal diameter of around 24-28 mm.

The pMDI further comprises a seat 5 for location of a drug canister 6 containing a respiratory drug at the junction between the upright portion 2 and the transverse mouthpiece 4. The canister 6 is inserted into the upright portion 2 of the body through the aperture 3 and is housed in the upright portion 2.

The upright portion 2 of the body further comprises a corrugated portion 7 which comprises a series of parallel ridges 8 and troughs 9. The ridges 8 and troughs 9 are integrally formed (moulded) into the inner surface of the upright portion 2 and are oriented substantially perpendicularly to the axis of the upright portion 2 and the air flow path.

The ridges 8 and troughs 9 partially encircle the air flow path and the canister 6 and extend the entire axial length of the upright portion 2 from immediately adjacent the aperture 3 to the junction with the transverse mouthpiece 4. The axial length of the corrugated portion 7 is approximately 30 mm and comprises nine ridges 8 and troughs 9 having a pitch of 3 mm.

The corrugated portion 7 comprises a lead-in ridge at its axial end proximal the aperture 3 such that as air first enters the corrugated portion 7 it is directed towards the axis of the upright portion 2 of the body by the inclined surface of the lead-in ridge.

The outer surface of the upright portion 2 is substantially smooth even in the area opposing the corrugated portion 7.

To use the pMDI 1, the patient will insert the mouthpiece 4 into their mouth and inhale. The air flowing into the upright portion 2 of the body through the aperture 3 will flow around the canister 6, over the corrugated portion 7 and into the transverse mouthpiece.

At the predetermined minimum flow rate which is the minimum air flow rate for optimal drug inhalation, the air drawn along the air flow path will become turbulent as a result of the air tumbling over the ridges 8 and troughs 9 of the corrugated portion 7. When the oscillations match the resonant frequency of the corrugated portion of the body, a sound signal having a narrow frequency width will be generated and the patient will know that the optimal inhalation rate has been achieved.

The generation of the sound signal may be detected by ear by the patient or the patient may be provided with software (e.g. in the form of a mobile phone app) to detect the generation of the sound signal and thus the attainment of the predetermined minimum flow rate for optimal drug delivery.

When the optimal inhalation rate has been achieved, the patient will then know to actuate the drug canister 6 to release the drug into the air flow path for inhalation. Actuation of the canister 6 is typically achieved by depressing the canister 6 into the upright portion 2 of the body. This causes an interaction between the canister 6 and the seat 5 that causes a metered dose of liquid to be ejected from the canister 6, along with a propellant gas. The liquid is aerosolized in the device, for inhalation by the patient. A drug of particular interest is salbutamol, marketed under the example trade names Ventolin™, Aerolin™, Ventorlin™ Asthalin™, Asthavent™, Proventil™ and ProAir™, for the management of asthma and other respiratory diseases.

The corrugated portion 7 is provided upstream (i.e. closer to the inlet aperture 2) than the seat 5 for location of the canister to avoid deposition of the respiratory drug into the troughs of the corrugated portion.

Upon depression of the canister 6, the frequency/pitch of the sound signal will change as a result of the change in the axial length/geometry of the corrugated portion 7. In situations where there is a desire to monitor patient compliance, the alteration in the frequency/pitch of the sound signal could be monitored/recorded (e.g. by the computer software/mobile app) to detect the point of actuation of the canister. The duration of the sound signal after actuation could also be monitored/recorded to help ensure that the optimal flow rate is maintained for a sufficient period of time after actuation.

Figure 2:
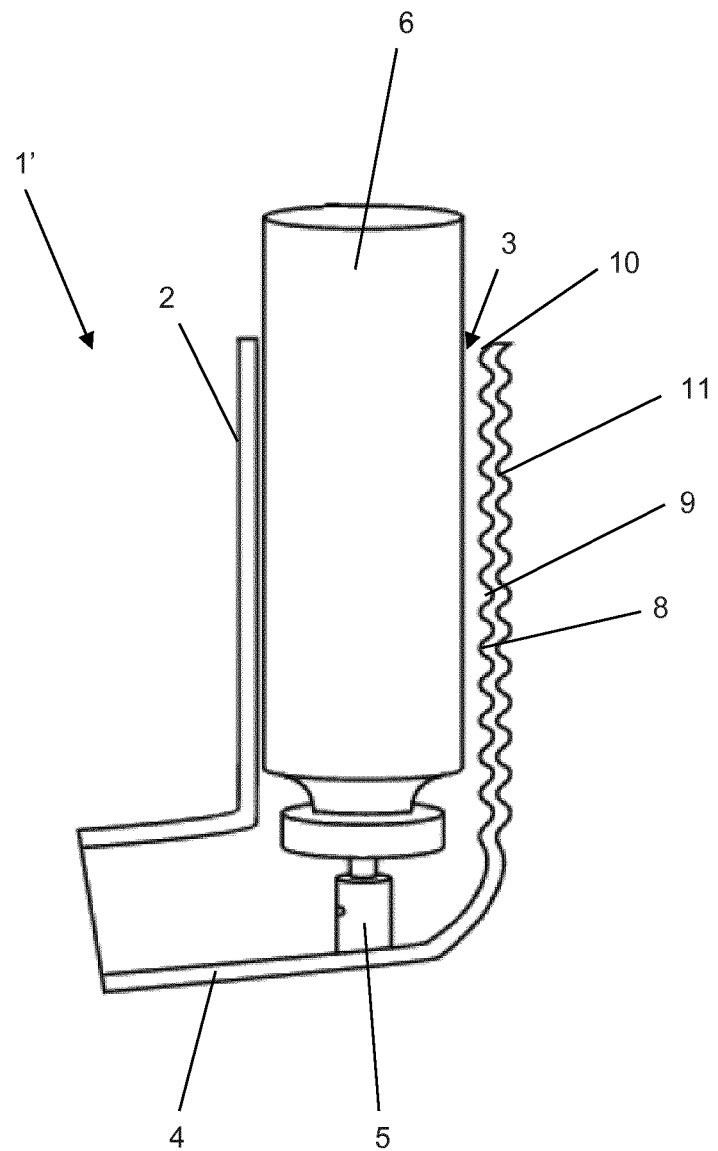
FIG. 2 shows a longitudinal cross-sectional view through a second embodiment of the present invention.
Figure 3:
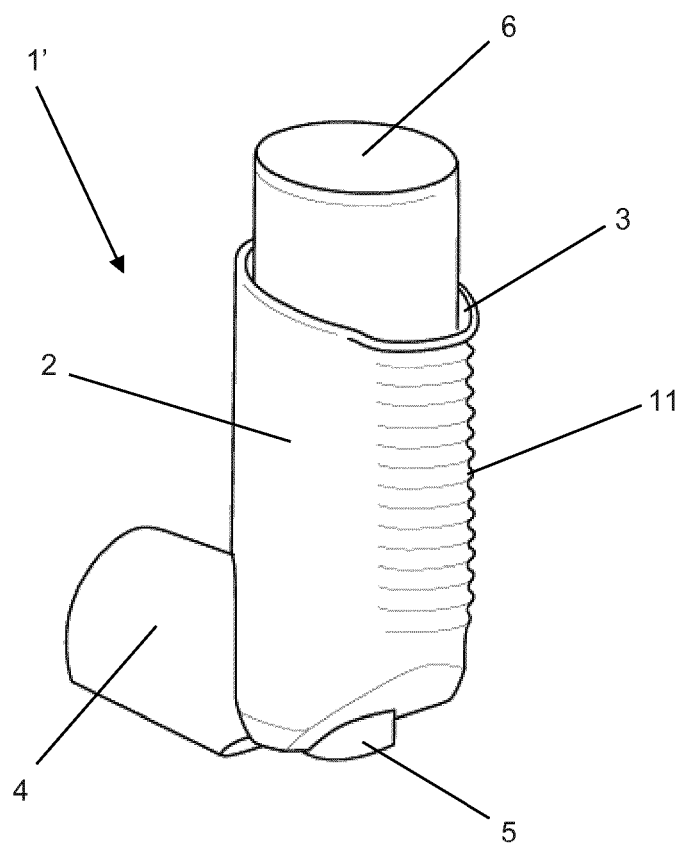
FIG. 3 shows a perspective view of the second embodiment.

FIGS. 2 and 3 show a second preferred embodiment of the pMDI inhaler 1' which is the same as that shown in FIG. 1 except the outer surface 11 of the upright portion 2 of the body is also provided with corrugations to provide a visual/tactile distinction for patients over the known pMDIs without the corrugated air flow rate indicator.

Figure 4:
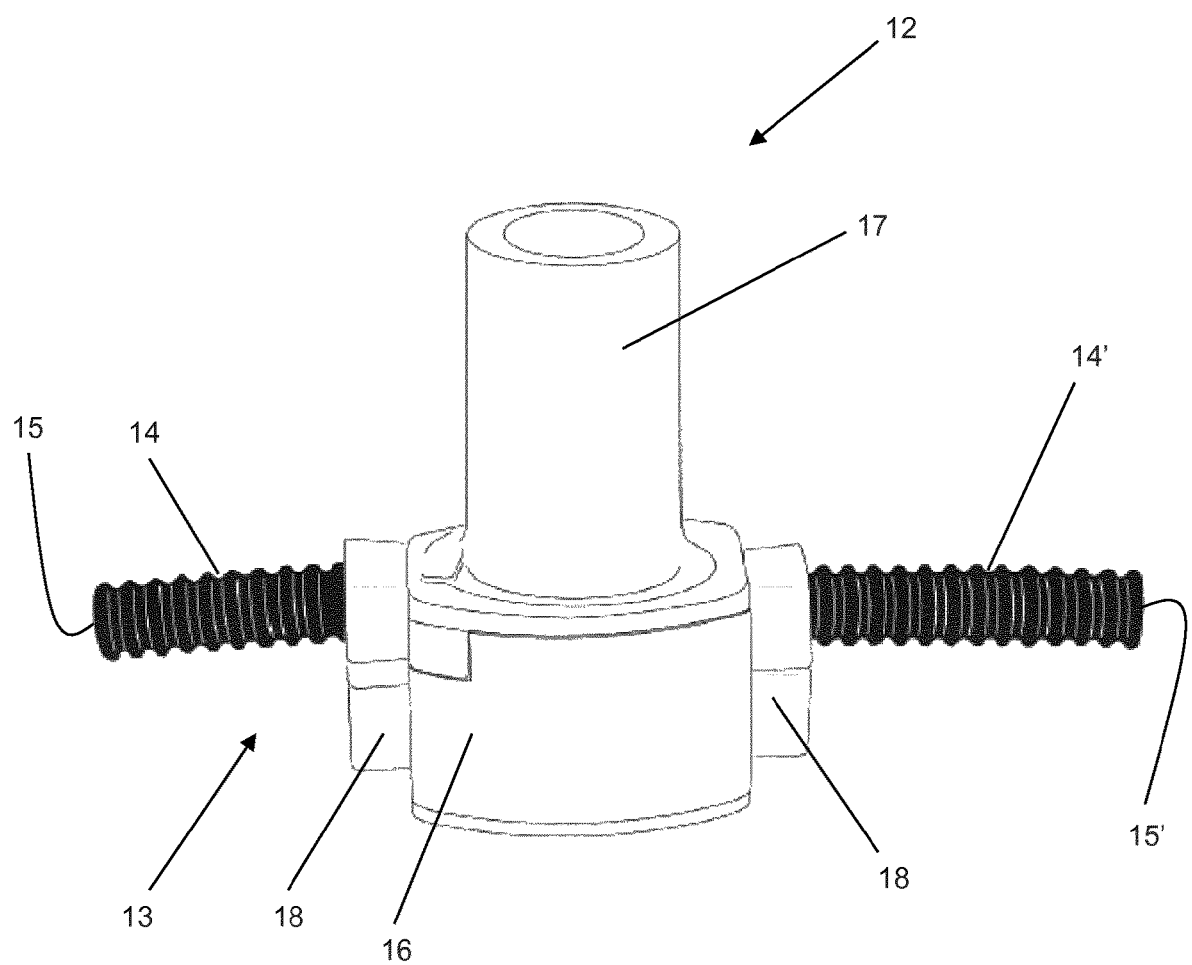
FIG. 4 shows a perspective view of a third embodiment.

FIG. 4 shows a third preferred embodiment of the present invention which is a DPI 12 adapted to deliver respiratory drugs to a patient. It is based upon a standard, commercially available DPI known as RS01 Monodose DPI, Plastiape S.p.a. The body 13 of the DPI is modified to comprise two tubular body portions 14, 14' each extending from a respective aperture 15, 15' to a main body portion 16 which defines two tubular channels (not shown) that extend to the location of a drug reservoir (e.g. a capsule in this case). The air flow path within the DPI extends from the apertures 15, 15' through the tubular body portions 14, 14', through the tubular channels (not shown) past the location of primed capsule to the mouthpiece 17 which is oriented substantially perpendicularly to the tubular channels/body portions 14, 14'.

The tubular body portions 14, 14' each form a corrugated portion and are provided with a plurality of ridges/troughs. The ridges and troughs are integrally formed (moulded) into the tubular body portions 14, 14' and are oriented substantially perpendicularly to the axis of the air flow path within the body. The ridges and troughs encircle the air flow path within the tubular body portions 14, 14'

One corrugated portion 14 has an axial length of 24 mm (with 23 ridges/troughs) and the other corrugated portion 14' has an axial length of 36 mm (with 34 ridges/troughs). Each tubular portion had an internal diameter of 5.2 mm.

In other embodiments (not shown), only one of the tubular body portions which form a corrugated portion is provided. In that embodiment, a second aperture 15' is provided in the main body portion 16 in fluid communication with the second tubular channel.

In other embodiments (not shown), instead of providing the tubular body portions, a corrugated portions may be provided within the or each tubular channel within the main body portion.

To use the DPI 1, the patient will prime the DPI to release the drug from the drug reservoir e.g. by squeezing actuator buttons 18, 18'. The patient will then insert the mouthpiece 4 into their mouth and inhale. The air flowing into the tubular body portions 14, 14' of the body through the apertures 15, 15' will flow over the ridges and troughs of the corrugated portions, into the tubular channels to the location of the primed capsule and then into the transverse mouthpiece 17.

At the predetermined minimum flow rate which is the minimum air flow rate for optimal drug inhalation, the air drawn along the air flow path will become turbulent as a result of the air tumbling over the ridges and troughs of the corrugated tubular body portions 14, 14'. When the oscillations match the resonant frequency of the corrugated portion(s), a sound signal having a narrow frequency width will be generated and the patient will know that the optimal inhalation rate has been achieved.

The generation of the sound signal may be detected by ear by the patient or the patient may be provided with software (e.g. in the form of a mobile phone app) to detect the generation of the sound signal and thus the attainment of the predetermined minimum flow rate for optimal drug delivery.

The corrugated tubular body portions 14, 14' are provided upstream (i.e. closer to the inlet apertures 15, 15') than the seat for location of the capsule to avoid deposition of the respiratory drug into the troughs of the corrugated portion.

Figure 5:
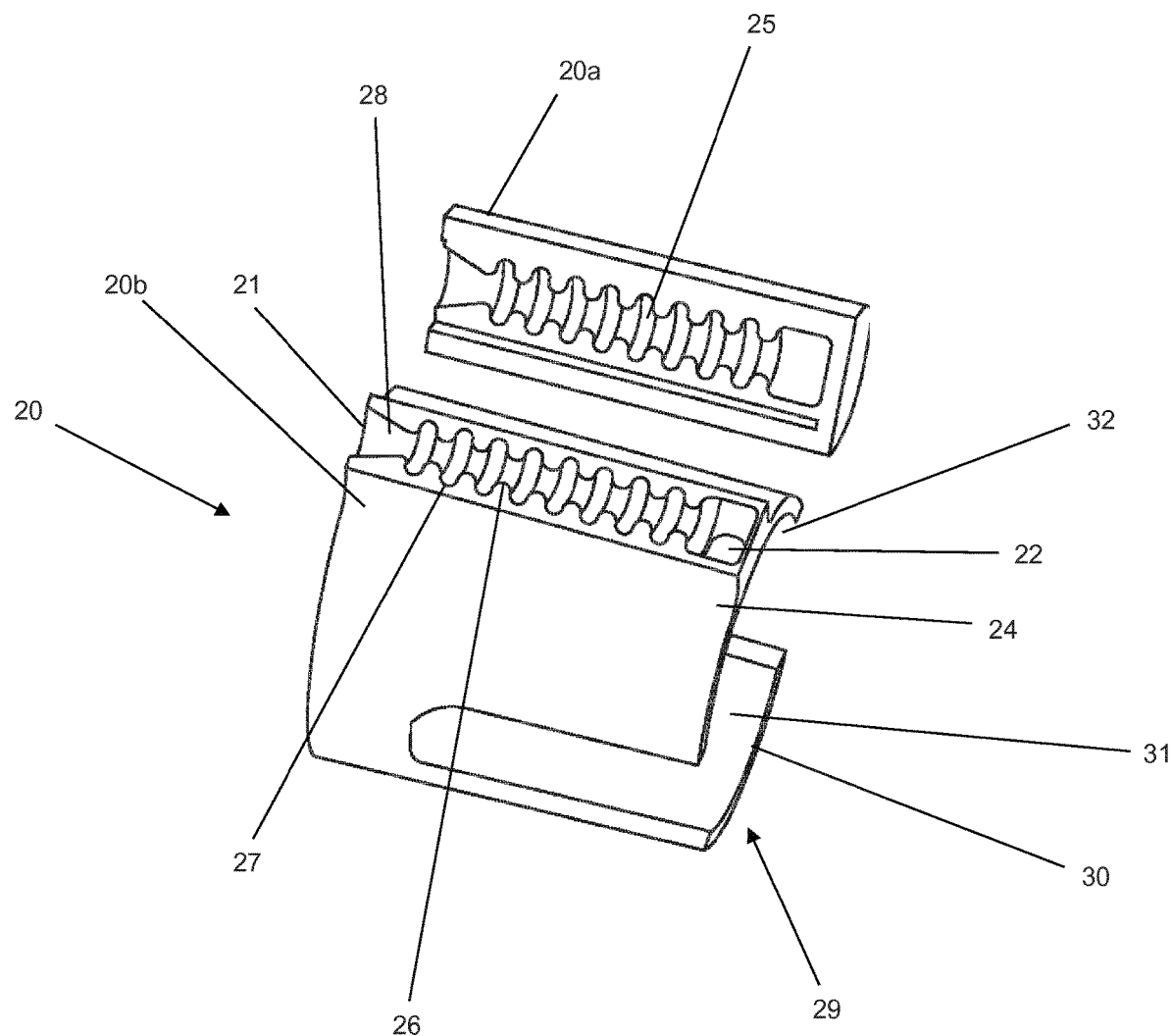
FIG. 5 shows a perspective view of a device according to the fourth aspect.
Figure 6:
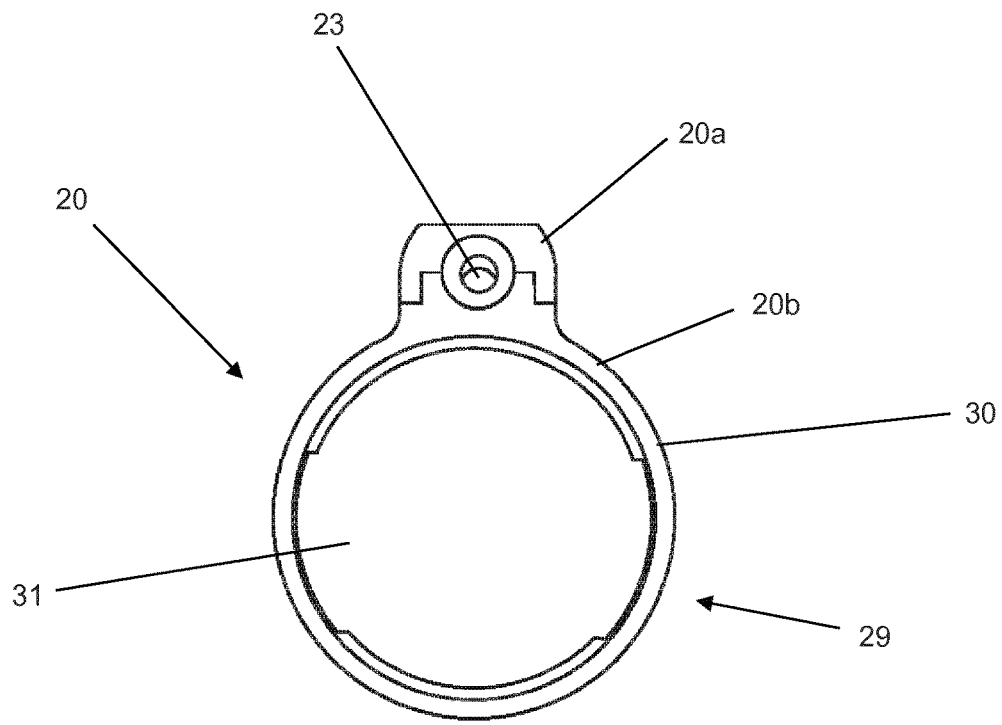
FIG. 6 shows a radial cross section of the device shown in FIG. 5.

FIGS. 5 and 6 show a device 20 for indicating a desired fluid flow rate along a fluid flow path through a respiratory inhaler (not shown).

Although the device is shown as having two parts 20a, 20b, this is for the ease of explanation and the two parts 20a, 20b may be integrally formed.

The device comprises an inlet aperture 21 for the inlet of air and an outlet aperture 22 with a second fluid flow path extending therebetween. The second fluid flow path (which has a circular radial cross-section) is defined within a tubular channel 23 formed within a body 24.

The inlet aperture 21 is an axial aperture i.e. aligned with the longitudinal axis of tubular channel 23 defining the second fluid flow path.

The inlet aperture 21 is defined by a funnel-shaped channel 28 with the maximum diameter of the funnel-shaped inlet provided distal the outlet aperture 22 such that air can be funnelled into the tubular channel 23 defining the second air flow path.

The outlet aperture 22 is a radial aperture i.e. it extends radially relative to the longitudinal axis of the tubular channel 23 defining the second fluid flow path.

A corrugated portion 25 is integrally formed into the inner walls of the tubular channel 23 and extends the entire length of the second fluid flow path from the funnel-shaped inlet aperture 21 to the outlet aperture 22.

The corrugated portion 25 comprises a plurality of parallel ridges/peaks 26 spaced by a plurality of troughs/furrows 27 which encircle the second fluid flow path. The plurality of ridges/troughs 26, 27 are oriented substantially perpendicularly to the second fluid flow path with the ridges 26 extending into the second fluid flow path.

The body 24 further comprises a connector portion 29 for connection to the respiratory inhaler which typically comprises a tubular inhaler body portion (not shown).

The connector portion 29 has a partial tubular sleeve 30 defining a tubular recess 31 within which the tubular inhaler body portion is received and retained e.g. by a friction fit. The tubular sleeve 30/tubular recess 31 has a longitudinal axis extending parallel to the longitudinal axis of the tubular channel 23 defining the second fluid flow path. The opening 32 within the tubular sleeve 30 may be used to assist in the insertion of the inhaler body into the tubular sleeve 30 of the device.

The device 20 shown in FIGS. 5 and 6 is intended for connection to a dry powder inhaler (DPI) such as Astra Zeneca's Turbohaler™.

The Turbohaler™ has an inhaler air flow path defined by a tubular inhaler body portion having an inhalation channel extending from a terminal air inlet at first axial end to a mouthpiece for communication with the mouth of the patient at the opposing axial end via the seat for the location of the drug source.

The tubular inhaler body portion also has a radial air inlet which admits further air into the inhaler air flow path to increase turbulence and therefore deagglomeration of the powdered drug. The radial air inlet is proximal the mouthpiece.

The tubular inhaler body portion of the Turbohaler™ is inserted into the tubular recess 31 defined by the tubular sleeve 31 via the opening 32 (or it may be simply slid into the recess 31).

The inlet aperture 21 of the device is located proximal the terminal air inlet of the Turbohaler whilst the outlet aperture 22 which opens into the recess 31 is aligned with the radial air inlet of the tubular inhaler body portion such that the tubular channel 23 is in fluid communication with the inhaler air flow path. The tubular channel 23 defining the second fluid flow path extends parallel to the tubular inhaler body portion.

Inhalation through the mouthpiece of the respiratory inhaler by the user draws air through the radial air inlet of the inhaler via the inlet aperture 21, the secondary flow path within the tubular channel 23 and the outlet aperture.

When the air flow rate along the second air flow path reaches a predetermined flow rate (which is obtained when a desired fluid flow rate along with inhaler air flow path is reached), the air flow over the corrugated portion 25 within the tubular channel 23 will become turbulent as a result of the air tumbling over the peaks 26 and troughs 27 of the corrugated portion 25. When the oscillations match the resonant frequency of the corrugated portion 25, a sound signal having a narrow frequency width will be generated and the patient will know that the optimal inhalation rate has been achieved and that they are inhaling correctly.

The generation of the sound signal may be detected by software (e.g. in the form of a mobile phone app) to detect the generation of the sound signal and thus the attainment of the predetermined minimum flow rate for optimal drug delivery. The FrequenSee™ app available as an Apple® and Android® app may, for example, be used for detecting the generation of the sound signal.

Figure 7:
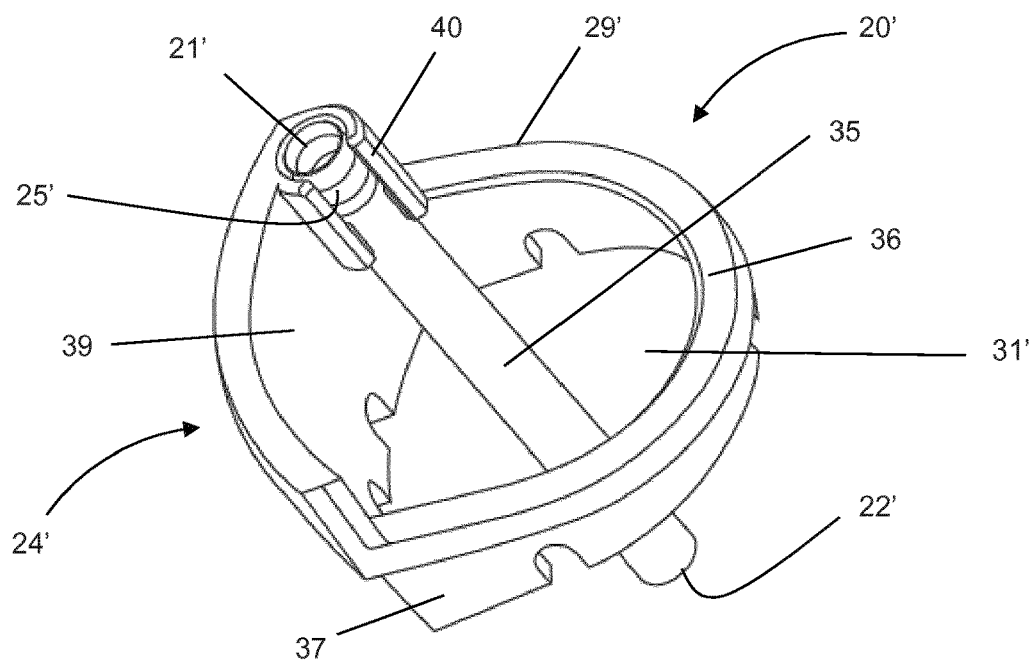
FIG. 7 shows a perspective view of a device according to the fourth aspect.
Figure 8:
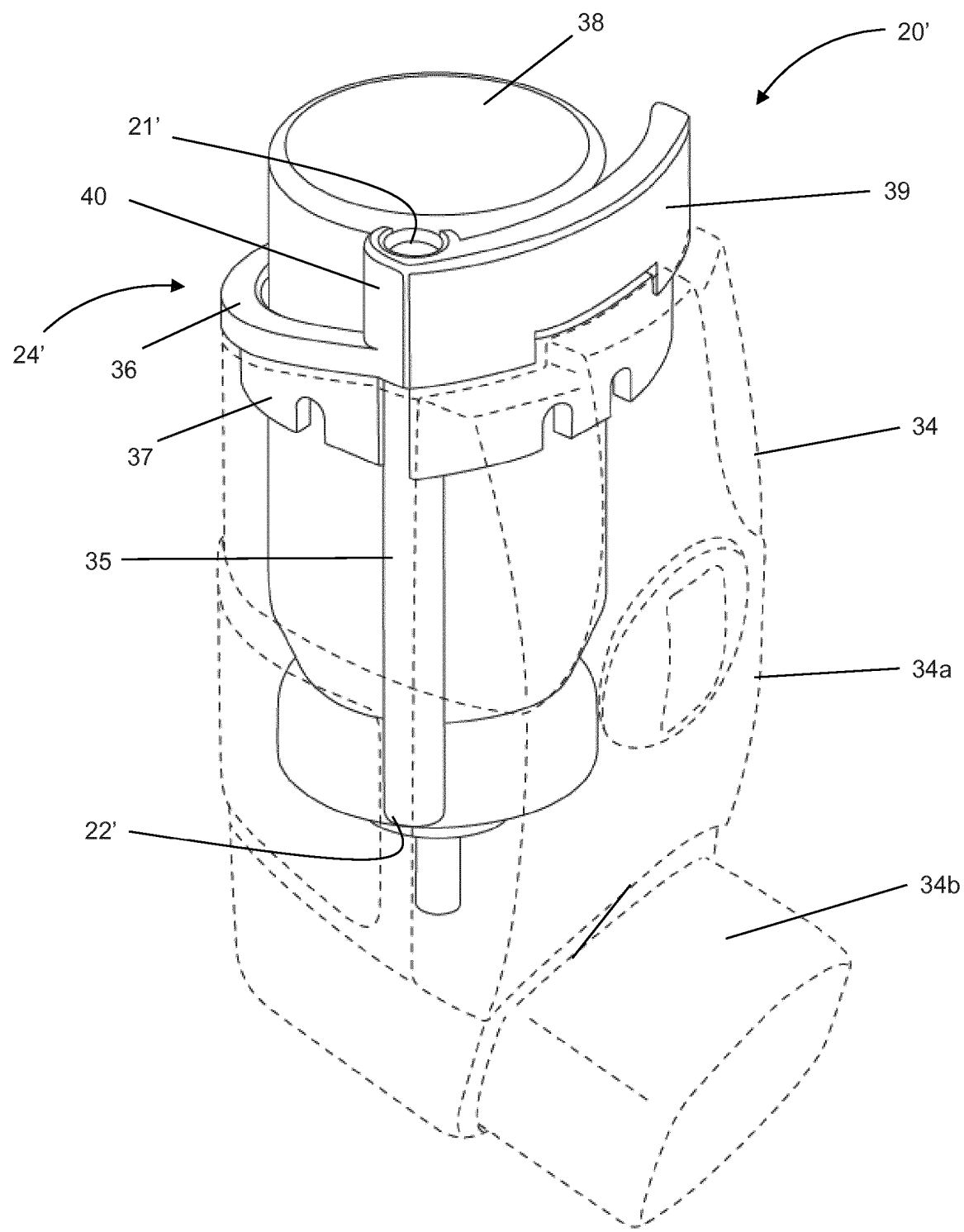
FIG. 8 shows a perspective view of the FIG. 7 device fitted to a pMDI.

FIGS. 7 and 8 show a device 20' for indicating a desired fluid flow rate along a fluid flow path through a respiratory inhaler 34 having an upright portion 34a and a transverse mouthpiece 34b. The inhaler shown is a Flutiform pMDI (Napp Pharmaceuticals) but the device 20' could be used with any conventional pMDI.

The device comprises an inlet aperture 21' for the inlet of air and an outlet aperture 22' with a second fluid flow path extending therebetween. The second fluid flow path (which has a circular radial cross-section) is defined within a tubular body portion 35.

A corrugated portion 25' is integrally formed into the inner walls of the tubular body portion 35 adjacent the inlet aperture.

The corrugated portion 25' comprises three parallel ridges/peaks spaced by troughs/furrows which encircle the second fluid flow path. The ridges/troughs are oriented substantially perpendicularly to the second fluid flow path with the ridges extending into the second fluid flow path. The remainder of the inner walls of the tubular body portion 35 are free of corrugations.

The body 24' further comprises a connector portion 29' for connection to the respiratory inhaler 34.

The connector portion 29' comprises a cap having an annular rim 36 with a downwardly depending skirt 37 which is received within and forms an interference fit with the upright portion of the respiratory inhaler 34. The annular rim defines a recess 31' through which a drug canister 38 can be inserted into the respiratory inhaler 34.

The connector cap 29' further comprises an upstanding tab 39 which comprises a clip 40 for receiving the tubular body portion 35. The clip 40 on the upstanding tab 39 grips the tubular body portion 35 with the inlet aperture 21' held at or above the height of the drug canister 38. This helps to prevent impedance of the inlet aperture by the drug canister 38.

The length of the tubular body portion 35 is such that the outlet aperture 22' is located above the valve seat (not shown) that receives the drug canister in the inhaler 34. Thus the outlet aperture is upstream of the point at which the drug in the drug canister 38 is aerosolised.

The outlet aperture 22' opens into the upright portion 34a of the pMDI body 34 and thus is in fluid communication with the inhaler air flow path.

Inhalation by the user draws air through the air inlet of the pMDI (between the annular rim 36 and the drug canister 38) and through the inlet aperture 21' of the tubular body portion 35 defining the second fluid flow path of the device.

When the air flow rate along the second fluid flow path reaches a predetermined flow rate (which is obtained when a desired fluid flow rate along with inhaler air flow path is reached), the air flow over the corrugated portion 25' in the tubular body portion 35 will become turbulent as a result of the air tumbling over the peaks and troughs of the corrugated portion 25'. When the oscillations match the resonant frequency of the corrugated portion 25' or the tubular body portion, a sound signal having a narrow frequency width will be generated and the patient will know that the optimal inhalation rate has been achieved and that they are inhaling correctly.

Figure 9:
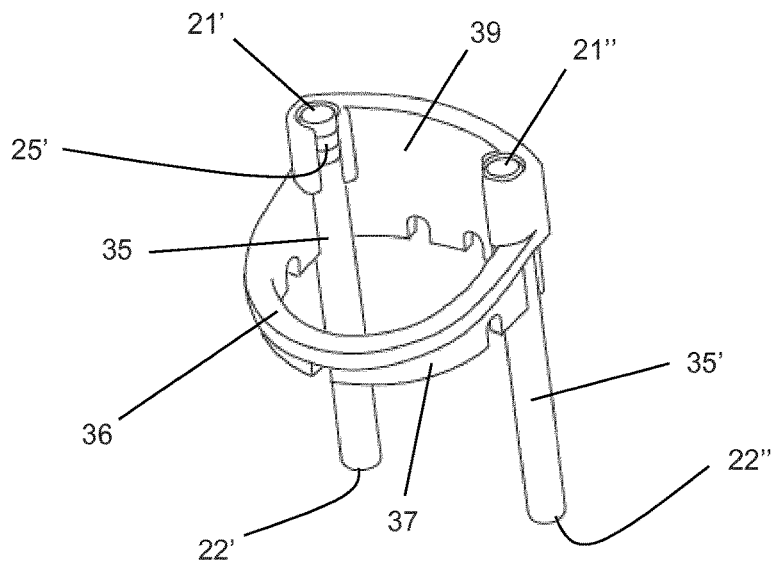
FIG. 9 shows a perspective view of a further device according to the fourth aspect.
Figure 10:
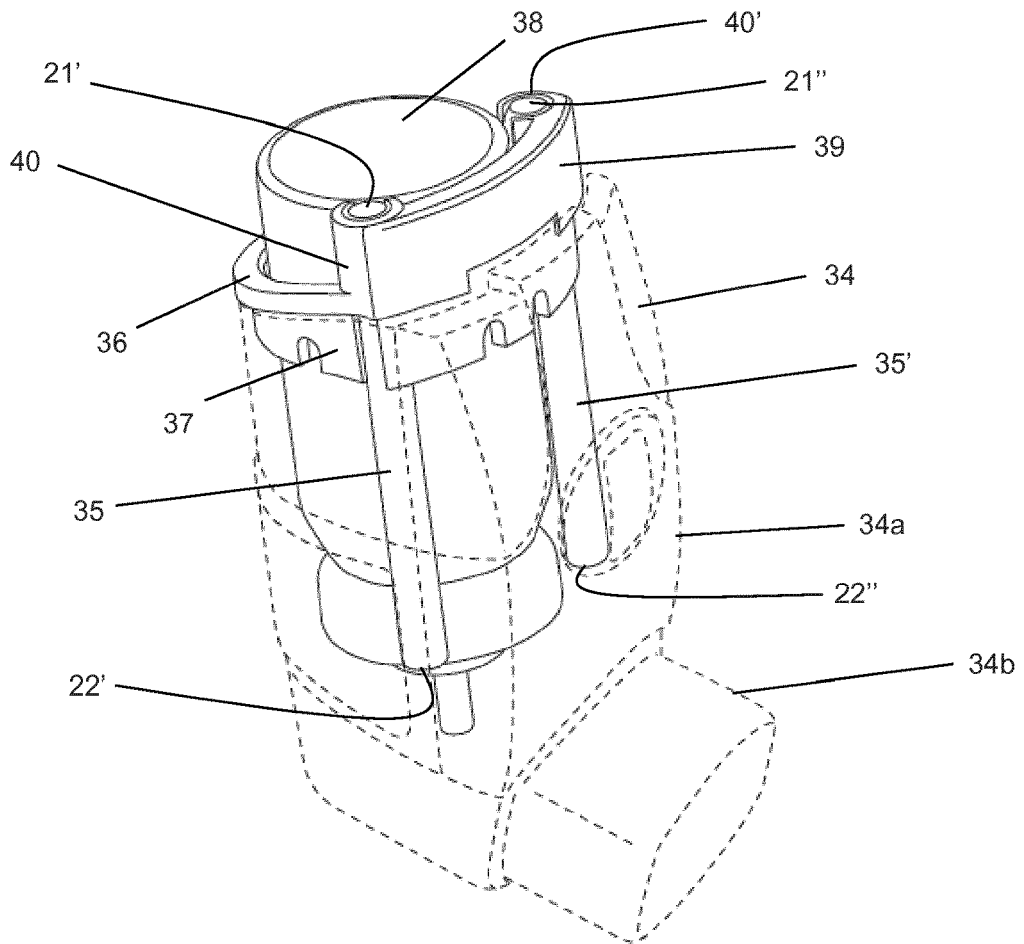
FIG. 10 shows a perspective view of the FIG. 7 device fitted to a pMDI.

FIGS. 9 and 10 show a further embodiment which is similar to that shown in FIGS. 7 and 8 except that a further tubular portion 35' having a further inlet aperture 21" and a further outlet aperture 22" and defining a further second fluid flow path is provided. The upstanding tab 39 comprises a further clip 40' for securing the further tubular body portion 35' within the upright portion 34a of the inhaler body 34. Although not visible, the corrugated portion in the further tubular body portion 35' has a greater number of corrugations than the corrugated portion of the tubular body portion 35 such that it generates an audible signal at a different flow rate through the further second fluid flow path than that at which a signal is generated in the second fluid flow path. In this embodiment where both tubular body portions 35, 35' have the same length and same diameter, the tubular body portion 35 (with fewer corrugations) is adapted to generate a sound signal at a predetermined flow rate that indicates a minimum optimal flow rate through the inhaler. The further tubular body portion 35' (which has more corrugations and therefore a greater flow resistance) is adapted to generate a sound signal at a predetermined flow rate that indicates a maximum optimal flow rate through the inhaler.

The generation of the sound signal(s) may be detected by software (e.g. in the form of a mobile phone app) to detect the generation of the sound signal and thus the attainment of the predetermined minimum flow rate for optimal drug delivery. The FrequenSee™ app available as an Apple® and Android® app may, for example, be used for detecting the generation of the sound signal.

EXPERIMENTAL DETAILS

Example 1

The pMDI inhaler shown in FIG. 1 was tested using a calibrated flow pump at increasing flow rates and the frequencies of the sound signal generated were measured using the smartphone app, FrequenSee™.

The results are shown in Table 1 below:

| Sound Frequency Display (Peak #) | Frequency of Sound (kHz) | Flow rate (L/min) |
|---|---|---|
| 1 | 1.9 | 22.5 |
| 2 | 3.5 | 34.0 |
| 3 | 3.8 | 38.0 |
| 4 | 4.0 | 45.0 |
| 5 | 4.8 | 60.0 * |

* limit of flow meter functional range

Accordingly, it can be seen that air flow over the corrugated portion at a flow rate of 22.5 L/min (which is the predetermined minimum flow rate for optimal drug delivery) results in the generation of a sound signal having a frequency of 1.9 kHz. As the air flow rate increases, further harmonics of the corrugated portion are detected at higher frequencies.

Example 2

The DPI inhaler shown in FIG. 4 was tested using a calibrated flow pump at increasing flow rates and the flow rates at which the sound signal was generated (detected using the smartphone app, FrequenSee™) were recorded. Tests were also carried out using versions of the DPI inhaler shown in FIG. 4 but only with a single corrugated tubular body portion (either the 24 mm or the 36 mm corrugated tubular body portion).

The results are shown in Table 2 below:

| | Corrugate | | |
|---|---|---|---|
| Flow rate (L/min) | single 26 mm tube | single 34 mm tube | both tubes |
| Whistle sounds | 21.9 | 23.7 | 40.0 |
| Whistle stops | 29.7 | 37.5 | * |

* beyond limit of test gauge used

The results show that the tailoring of the axial length of the corrugated portion can be used to modify the flow rate at which the sound signal is generated. Using two corrugated portions increases the resistance through the device such that a higher flow rate is needed to generate the sound signal.

Example 3

Figure 11:
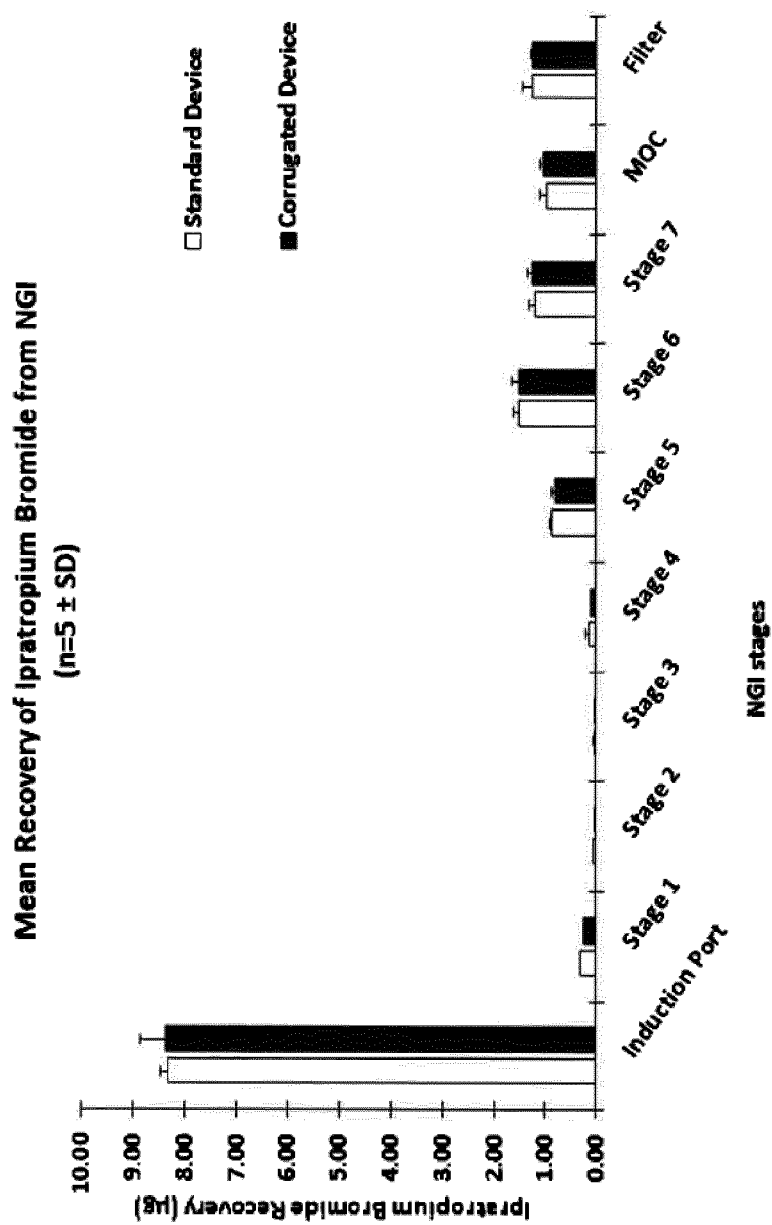
FIG. 11 shows a bar chart of particle size distribution for a standard pMDI inhaler device compared with a pMDI inhaler device as shown in FIG. 1.

The performance of an aerosol containing 20 μg ipratropium bromide per actuation (Atrovent®) delivered using a standard pMDI inhaler device was compared with a pMDI inhaler device as shown in FIG. 1. The in vitro evaluation used a Next Generator Impactor (NGI), with all apparatus and devices operated under standard conditions, using recommended procedures and analytical protocols. Particle size distributions (see FIG. 11) and aerosol performance (Table 3) of the standard device and the device containing the corrugations were similar.

The aerosol performance results are shown in Table 3 below

|  | Standard Device | Corrugated Device |
|---|---|---|
| Metered Dose (µg) | 18.41 ± 0.34 | 18.38 ± 0.29 |
| Emitted Dose (µg) | 14.78 ± 0.39 | 14.85 ± 0.34 |
| Fine Particle Fraction (% < 5 µm) | 40.96 ± 2.44 | 41.36 ± 2.09 |
| Fine Particle Dose (µg < 5 µm) | 6.06 ± 0.52 | 6.14 ± 0.22 |
| µg of drug on Actuator | 3.63 ± 0.20 | 3.53 ± 0.17 |

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A device for indicating a desired fluid flow rate along a fluid flow path through a respiratory inhaler, the device comprising:
    an inlet aperture;
    an outlet aperture for fluid communication with the fluid flow path through the respiratory inhaler; and
    a body defining a second fluid flow path extending between the inlet aperture and the outlet aperture, the body comprising:
        a connector portion for connection to the respiratory inhaler; and
        a fluid flow rate indicator operable to generate a sound signal to indicate when the fluid flow rate along the second fluid flow path is at a predetermined fluid flow rate,
wherein the fluid flow rate indicator comprises a corrugated portion having a plurality of corrugations extending into the second fluid flow path, wherein the corrugated portion comprises a plurality of parallel ridges/peaks spaced by a plurality of curved troughs/furrows which at least partially encircle the second fluid flow path.

2. A device according to claim 1 wherein the body comprises a substantially tubular channel or substantially tubular body portion defining a substantially tubular second fluid flow path and wherein the corrugated portion is integrally formed with the inner walls of the tubular channel/body portion.

3. A device according to claim 1 wherein the plurality of ridges/troughs are oriented substantially perpendicularly to the second fluid flow path.

4. A device according to claim 1 wherein the connector portion has a tubular recess defined by a full or partial tubular sleeve within which the respiratory inhaler may be received and retained and wherein the outlet aperture of the second fluid flow path opens into the recess of the connector portion.

5. A device according to claim 2 wherein the connector portion is a cap for seating on the respiratory inhaler and for mounting the tubular body portion within the inhaler air flow path.

6. A device according to claim 1 wherein the body defines a further second fluid flow path extending between a further inlet aperture and a further outlet aperture, and a further fluid flow rate indicator operable to generate a further sound signal to indicate when the fluid flow rate along the further second fluid flow path is at a second predetermined fluid flow rate, wherein the further fluid flow rate indicator comprises a further corrugated portion having at least one corrugation extending into the further second fluid flow path.

7. A device according to claim 1, the device comprising:
    a tubular body portion defining the second fluid flow path extending between the inlet aperture and the outlet aperture, the corrugated portion having at least one corrugation extending into the second fluid flow path within the tubular body portion and a further tubular body portion defining a further second fluid flow path extending between a further inlet aperture and a further outlet aperture, and a further fluid flow rate indicator operable to generate a further sound signal to indicate when the fluid flow rate along the further second fluid flow path is at a second predetermined fluid flow rate, wherein the fluid flow rate indicator comprises a further corrugated portion having at least one corrugation extending into the further second fluid flow path, and wherein the two flow rate indicators have a different number of corrugations and/or the two tubular body portions have different path lengths.

8. A system comprising a device according to claim 1 and a sound receiver for detecting the sound signal.

9. A method of monitoring actuation of a respiratory inhaler device for delivery of a drug to a patient, the method comprising:
    providing a system according to claim 8,
    detecting the sound signal generated when the air flow rate along the air flow path is at or above the predetermined minimum level suitable for delivery of the drug to the patient,
    detecting a change in frequency of the sound signal upon actuation of the device by the patient.

10. A device for indicating a predetermined fluid flow rate, the device comprising:
    an aperture;
    a mouthpiece; and
    a body defining a fluid flow path extending between the aperture and the mouthpiece, the body comprising a fluid flow rate indicator operable to generate a sound signal to indicate when the fluid flow rate along the fluid flow path is at the predetermined fluid flow rate,
    wherein the fluid flow rate indicator comprises a corrugated portion having a plurality of corrugations extending into the fluid flow path, wherein the corrugated portion comprises a plurality of parallel ridges/peaks spaced by a plurality of curved troughs/furrows which at least partially encircle the fluid flow path.

11. A device according to claim 10 wherein the body and/or corrugated portion is substantially rigid.

12. A device according to claim 10 wherein the plurality of ridges/troughs are oriented substantially perpendicularly to the fluid flow path.

13. A device according to claim 10 wherein the device is a patient inhalation/exhalation device and wherein:
    the aperture is for inlet or outlet of air into/from the device;
    the mouthpiece is for communication with the mouth of the patient;

the fluid flow path is an air flow path extending between the aperture and the mouthpiece along which air is drawn to the mouthpiece by inhalation by the patient or air is forced towards the aperture by exhalation by the patient and the fluid flow rate indicator is an air flow rate indicator operable to generate a sound signal to indicate when the air flow rate along the air flow path is at or above a predetermined minimum level.

14. A device according to claim 13 wherein the device is a respiratory inhaler device for delivery of a drug to a patient, and wherein:
the aperture is for inlet of air into the device; and
the fluid flow path is an air flow path extending from the aperture to the mouthpiece along which air is drawn to the mouthpiece by inhalation by the patient and the fluid flow rate indicator is an air flow rate indicator operable to generate a sound signal to indicate when the air flow rate along the air flow path is at or above a predetermined minimum level suitable for delivery of the drug to the patient.

15. A device according to claim 14 wherein the inhaler device further comprises a seat for location of a drug reservoir and the corrugated portion is provided upstream than the seat for location of the drug reservoir.

16. A device according to claim 13 wherein the device is a spacer or holding chamber for a respiratory inhaler for delivery of a drug to a patient, wherein:
the aperture is adapted to receive a mouthpiece of the respiratory inhaler; and
the fluid flow path is an air flow path extending from the aperture to the mouthpiece of the device along which air is drawn to the mouthpiece of the device by inhalation by the patient and the flow rate indicator is an air flow rate indicator operable to generate a sound signal to indicate when the air flow rate along the air flow path is at or above a predetermined minimum level suitable for delivery of the drug to the patient.

17. A device according to claim 16 wherein the body is tubular and comprises an axially oriented recess wherein the corrugated portion is provided in the axially-oriented recess.

18. A system comprising a device according to claim 10 and a sound receiver for detecting the sound signal.

* * * * *